(12) United States Patent
Rothenpieler et al.

(10) Patent No.: US 7,612,046 B2
(45) Date of Patent: Nov. 3, 2009

(54) METHOD FOR TREATING KIDNEY DISORDERS

(76) Inventors: Uwe Waldemar Rothenpieler, Vetterstr. 22, 86609 Donauworth (DE); Michael Carl Elmar Imgrund, Stadstr. 1, 79104 Freiburg (DE)

( * ) Notice: Subject to any disclaimer, the term of this patent is extended or adjusted under 35 U.S.C. 154(b) by 230 days.

(21) Appl. No.: 10/182,680

(22) PCT Filed: Jan. 31, 2001

(86) PCT No.: PCT/EP01/01004

§ 371 (c)(1),
(2), (4) Date: Sep. 27, 2002

(87) PCT Pub. No.: WO01/54706

PCT Pub. Date: Aug. 2, 2001

(65) Prior Publication Data

US 2003/0124093 A1    Jul. 3, 2003

Related U.S. Application Data

(60) Provisional application No. 60/179,129, filed on Jan. 31, 2000.

(51) Int. Cl.
| | |
|---|---|
| A01N 43/04 | (2006.01) |
| C12N 15/00 | (2006.01) |
| C12N 15/63 | (2006.01) |
| C07H 21/04 | (2006.01) |
| A01N 63/00 | (2006.01) |

(52) U.S. Cl. ................... 514/44; 424/93.21; 435/320.1; 435/455; 536/23.5

(58) Field of Classification Search ................ 536/23.1, 536/23.5; 514/44; 530/350; 435/325, 320.1, 435/455; 424/93.21
See application file for complete search history.

(56) References Cited

U.S. PATENT DOCUMENTS

| 5,360,790 | A | 11/1994 | Humes |
| 5,750,495 | A | 5/1998 | Woo |
| 5,882,923 | A | 3/1999 | Sariola et al. |
| 2003/0092657 | A1* | 5/2003 | Goodyer et al. ............... 514/44 |

FOREIGN PATENT DOCUMENTS

| EP | 0 853 942 A | 7/1999 |
| WO | WO 98/41227 A | 9/1998 |
| WO | WO 98/50060 A | 11/1998 |

OTHER PUBLICATIONS

Anglani et al. (2004) In search of adult renal stem cells. J. Cell. Mol. Med. 8:474-487.*
Sandall. (2000) Genes and Gene Expression. Clin. Orth. and Rel. Res. 379S:S9-S16.*
Zhang et al. (2004) Angiotensin II stimulates Pax-2 in rat kidney proximal tubular cells: Impact on proliferation and apoptosis.*
Daniel et al. (2001) Pax-2 expression in Adult renal Tumors. 32:282-287.*
Tavassoli et al. (1997) Alternative splicing in Pax2 generates a new reading frame and an extended conserved coding region at the carboxy terminus. Hum Genet. 101:371-375.*
Abbattista et al. (2004) Stem Cells and Kidney diseases. Minerva Medica. 95:411-8.*
Johnson-Saliba et al. (2001) Gene Therapy:optimising DNa delivery to the nucleus. Curr. Drug Targets 2:371-99.*
Verma et al., Gene therapy-promises, problems and prospects. (1997) Nature. 389:239-242.*
Ritz-Laser et al. (2000) The paired homeodomain transcription Factor Pax-2 is expressed in the endocirine pancreas and transactivates the glucagon gene promoter. J. Biol. Chem. 275:32708-32715.*
Hopes Glossary (2005) R. pp. 1-4. Http://www.stanford.edu/group/hopes/sttools/gloss/r.html.*
Shoji et al. (2004) Current Status of Delivery systems to improve Target Efficacy of Oligonucleotides. Curr. Pharm. Design 10:785-796.*
Pfeifer and Varmus (2001) Gene Therapy: Promises and Problems Annu. Rev. Genomics Hum. Genet. 2:177-211.*
Greco et al. (2002) Cancer Gene therapy:'Delivery, Delivery, Delivery'. Frontiers in Bioscience. 7:d1516-1524.*
Yokoo et al. (2003) Stem Cell Gene Therapy for Chronic Renal Failure. Curr. Gene Therapy. 3:387-394.*
Deonarain, M., 1998, Expert Opin. Ther. Pat., vol. 8, pp. 53-69.*
Verma et al., Sep. 1997, Nature, vol. 389, pp. 239-242.*
Eck et al., 1996, Goodman & Gilman's The Pharmacological Basis of Therapeutics, McGraw-Hill, New York, p. 77-101.*
Gorecki, D., 2001, Expert Opin. Emerging Drugs, 6(2): 187-198.*
Rudinger, 1976, Peptide Hormones, Parsons, University Park Press, Baltimore, p. 1-7.*
Kaye et al., 1990, Proc. Natl. Acad. Sci. USA, vol. 87, pp. 6922-6926.*
Skolnick et al., 2000, Trends in Biotech, vol. 18, p. 34-39.*
McConnell et al., 1997, Oncogene, vol. 14, p. 2689-2700.*
Luo et al., "BMP-7 is an inducer of nephrogenesis and is also required for eye development and skeletal patterning," Genes 7 Development (1995), vol. 9, No. 22, pp. 2808-2820, SP001015455, ISSN: 0890-9369.

(Continued)

*Primary Examiner*—Shin-Lin Chen
(74) *Attorney, Agent, or Firm*—Foley & Lardner LLP

(57) ABSTRACT

The present invention relates to a cellular therapy of renal failure, i.e. preventing, delaying, and treating acute/chronic renal failure via the use of an effective dose of a substance capable of inducing and/or enhancing Pax2 expression in a mammal for the preparation of a pharmaceutical composition for treating, preventing or delaying a renal dysfunction/failure in a mammal. Additionally, the present invention provides for a method for converting mesenchymal tissue into an epithelial tissue comprising the administration of an effective amount of a substance capable of inducing and/or enhancing Pax2 expression in mesenchymal tissue and for a method for the regeneration of renal stem cells comprising the administration of an effective amount of a substance capable of inducing and/or enhancing Pax2 expression.

8 Claims, 7 Drawing Sheets

OTHER PUBLICATIONS

Figure 1:
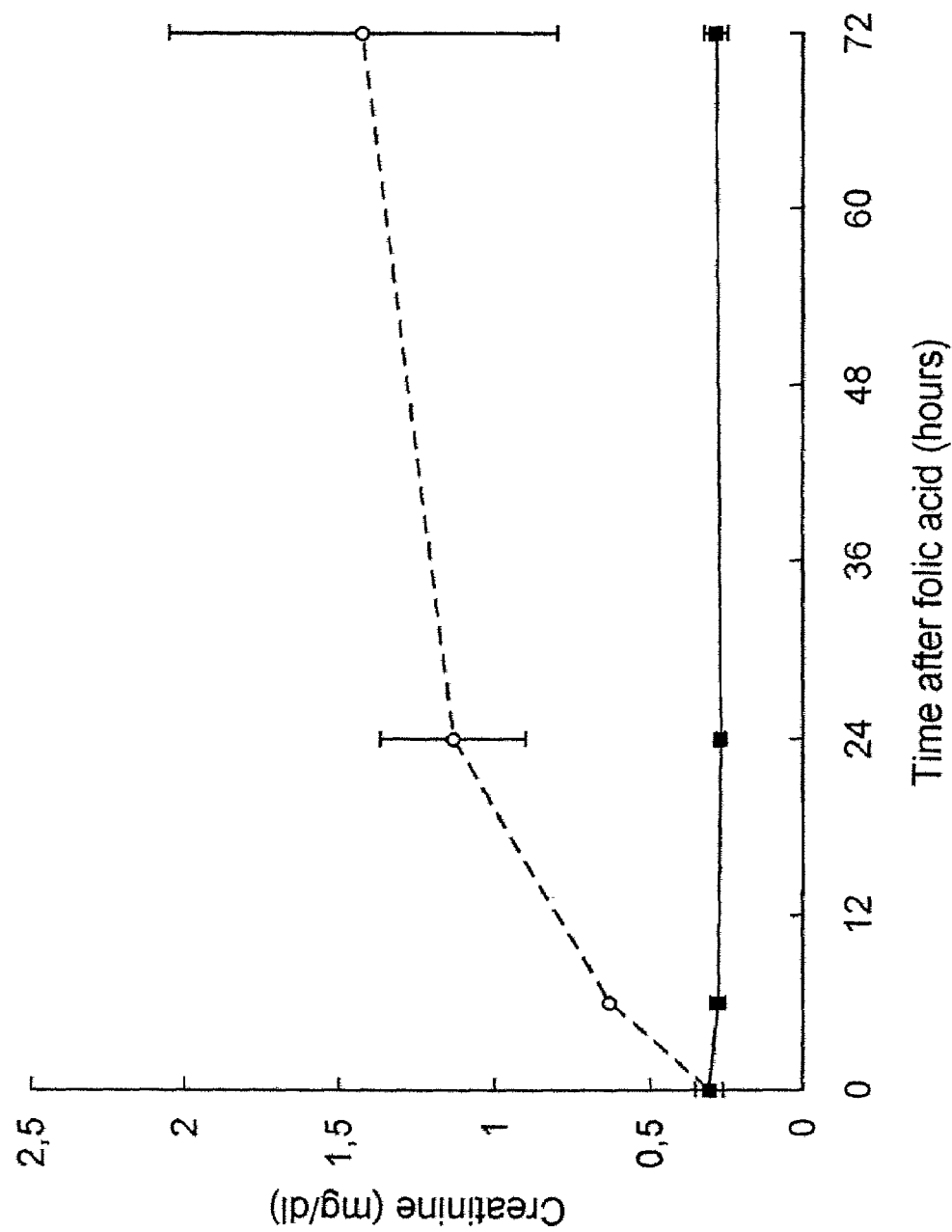

Cale et al., "Tumor necrosis factor-alpha inhibits epithelial differentiation and morphogenesis in the mouse metanephric kidney in vitro," *International Journal of Developmental Biology* (Jul. 1998), vol. 42, No. 5, pp. 663-674, XP001015477, ISSN: 0214-6282.

Eccles, "The role of Pax2 in Normal and Abnormal Development of the Urinary Tract," *Pediatric Nephrology* (1998), vol. 12, No. 9, pp. 712-720, XP001009818, ISSN: 0931-041X, Springer Verlag, Berlin, Germany.

Imgrund et al., "Re-expression of the developmental gene Pax-2 during expreimental acute tubular necrosis in mice," *Kidney International* (Oct. 1999), vol. 56, No. 4, pp. 1423-1431, XP002174276, ISSN: 0085-2538.

Barasch et al., "Mesenchymal to epithelial conversion in rat metanephros is induced by LIF," *Cell* (Nov. 12, 1999), vol. 99, No. 4, pp. 377-386, XP002174277, ISSN: 0092-8674.

Herzlinger et al., "Wnt-1 and Wnt-2 are potent inducers of nephrogenesis," *FASEB Journal* (1994), vol. 8, No. 4-5, p. A822, XP00217428, ISSN: 0892-6638.

Stark et al., "Epithelial transformation of metanephric mesenchyme in the developing kidney regulated by Wnt-4," *Nature* (Dec. 15, 1994), vol. 372, No. 6507, pp. 679-683, XP002130718, ISSN: 0028-0836, MacMillan Journals Ltd., London, Great Britain.

Torban et al., "Effects of PAX2 Expression in a Human Fetal Kidney (HEK293) Cell Line," *Biochimica Et Biophysica Acta* (1998), vol. 1401, pp. 53-62, XP001009827, ISSN: 0006-3002, Amsterdam, Netherlands.

Davies et al., "Induction of early stages of kidney tubule differentiation by lithium ions," *Developmental Biology* (1995), vol. 167, No. 1, pp. 50-60, XP001015458, ISSN: 0012-1606.

Padanilam et al., "Insulin-like growth factor I-enhanced renal expression of ostenpontin after acute ischemic injury in rats," *Endocrinology* (1996), vol. 137, No. 5, pp. 2133-2140, XP001015470, ISSN: 0013-7227.

Basile et al., "Expression of bcl-2 and bax in regenerating rat renal tubules following ischemic injury," *American Journal of Physiology* (1997), vol. 272, No. 5, part 2, pp. F640-F647, XP001015457, ISSN: 002-9513.

Dressler et al., "Pax-2 is a DNA-binding protein expressed in embryonic kidney and Wilms tumor", Proc. Natl. Acad. Sci., USA, vol. 89, pp. 1179-1183, Feb. 1992 (Developmental Biology).

Cai et al., "Groucho suppresses Pax2 transactivation by inhibition of JNK-mediated phosphorylation", The EMBO Journal, Vo. 22, No. 20, pp. 5522-5529, 2003.

(Abstract) Humes et al., "Tubulogenesis from isolated single cells of adult mammalian kidney: clonal analysis with a recombinant retrovirus", Am. J. Physiol., Jul. 1996, 271, F42-9).

(Abstract) Tavassoli et al., "Alternative splicing in PAX2 generates a new reading frame and an extended conserved coding region at the carboxy terminus", Hum Genet. Dec. 1997: 101(3):371-5.

(Abstract) Havik et al., "A novel paired domain DNA recognition motif can mediate Pax2 repression of gene transcription" Biochem Biophys Res Commun. Dec. 20, 1999, 266(2):532-41.

Chan et al., (2005) Tubular expression of angiotensin II receptors and their regulation in IgA nephropathy. J Am Soc Nephrol 16, 2306-17.

Havik et al., Biochem Biophys Res Commun Dec. 20, 1999:266(2):532-41.

Humes et al., Am J. Physiol., Jul. 1996:(271(1 Pt 2):F42-9.

Zhang et al., (2004b) Angiotensin II stimulates Pax-2 in rat kidney proximal tubular cells: impact on proliferation and apoptosis. Kidney Int 66, 2181-2192.

Zhang et al., JR (2004a) Angiotensin II increases Pax-2 expression in fetal kidney cells via the AT2 receptor. J Am Soc Nephrol 15, 1452-1465.

\* cited by examiner

METHOD FOR TREATING KIDNEY DISORDERS

The present invention relates to a method for treating, delaying and/or preventing renal dysfunction/failure in a mammal comprising administering a therapeutically effective amount of a substance capable of inducing and/or enhancing Pax2 expression. Furthermore, the invention relates to the use of an effective dose of a substance capable of inducing and/or enhancing Pax2 expression in a mammal for the preparation of a pharmaceutical composition for treating, preventing or delaying a renal dysfunction/failure in a mammal. Additionally, the present invention provides for a method for converting mesenchymal tissue into an epithelial tissue comprising the administration of an effective amount of a substance capable of inducing and/or enhancing Pax2 expression in said mesenchym and for a method for the regeneration of renal stem cells comprising the administration of an effective amount of a substance capable of inducing and/or enhancing Pax2 expression Several documents are cited throughout the text of this specification. Each of the documents cited herein (including any manufacturer's specifications, instructions, etc.) are hereby incorporated by reference.

The early development and differentiation of the mammalian metanephric kidney is accompanied by the induced differentiation of mesenchymal cells into a small stem cell population that differentiates and undergoes a mesenchymal to epithelial transition (Bard (1994), Mech. Dev. 48: 3-11). This process is supported by signals derived from the ureteric bud at a stage when the bud is moving out of the mesonephric duct (Lechner and Dressler (1997), Mech. Dev. 62: 105-120; Dressler (1999), *Dev. Gen.* 24: 189-193).

Acute tubular necrosis (ATN) is, with prerenal disease, one of the two most common causes of acute renal failure. It accounts for two thirds of intrinsic causes of acute renal failure. For example, about 5% of all hospitalized patients (regarding Germany ca. 725,000 of 14,321,321 patients being treated; statistics of 1998 according to the "Bundesgesundheitsamt" in Bonn, Germany) develop an ATN (Hou (1983), Am. J. Med. 74, 243-248), which is connected with a high mortality rate of about 50-60% (Bartlett (1984), Am. Soc. Artif. Intern. Organs 30, 700-702). The molecular basis of events leading to tubular regeneration after ATN is incompletely understood. An attractive hypothesis claims, that regeneration processes recapitulate developmental paradigms in order to restore organ or tissue function (Bacallao (1989), Am. J. Physiol. 257: F913-F924; Wallin (1992), Lab. Invest. 66: 474-484) This hypothesis can be tested by looking for similarities between developmental and regenerative processes on a molecular level during experimental ATN.

The adult tubular epithelium has a great potential of regeneration after damage, which distinguishes it from other tissues such as brain or heart. During ATN normally quiescent cells undergo dedifferentiation and re-obtain their potential to divide after greatly enhancing their rate of DNA-synthesis (Taylor (1966), Nature 212: 472-474, 966; Safirstein (1990), Kidney Int. 37: 1515-1521). After proliferation the new cells differentiate in order to restore the functional integrity of the nephron.

Expression and bioactivity of growth factors can be regulated by transcription factors (Dey (1994), Mol. Endocrinol. 8: 595-602). The expression of growth factors such as HGF and IGF-1 has been shown to be upregulated after artificial kidney damage, while EGF expression is downregulated. Amongst other genes, whose expression is upregulated after ATN, are immediate early genes like c-fos, c-myc, c-jun or EGR-1 (for review see 6). Kid-1 is a zinc finger gene which is not expressed in embryonic kidneys although there is specific expression in adult kidneys (Witzgall (1993), Mol. Cell Biol. 13: 1933-1942). Since the expression of Kid-1 is lost in proximal tubules of folic acid treated animals (Witzgall (1993), Mol. Cell Biol. 13: 1933-1942), its downregulation may reflect a functional stage similar to early kidney development. Other examples demonstrating the biological importance of biphasic protein expression during development and adulthood include the expression of bcl-2 and bax, which during early metanephric development are known for their antiapoptotic and proapoptotic roles, respectively (Veis (1993), Cell 75: 229-240; Knudson (1995), Science 270: 96-99). During adulthood they have been shown to be reexpressed in proximal tubular cells after ischemic damage (Basile (1997), Am. J. Physiol. 272: F640-F647). Vimentin is an intermediate filament and a marker of undifferentiated mesenchymal cells. It is not present in the healthy adult tubule but re-expression occurs during tubular regeneration (Wallin (1992), Lab. Invest. 66: 474-484). These examples are consistent with the hypothesis that during regeneration the cascade of developmental gene pathways may be reactivated. However, the expression pattern of a transcription factor which is transiently expressed during nephrogenesis and which is supposed to be part of the genetic cascade leading to proper kidney regeneration in adulthood after kidney damage are not examined and the potential developmental genes are not known.

U.S. Pat. No. 5,747,250 describes novel agents for tumor diagnosis and/or tumor therapy which comprise certain "homeobox" transcription factors. These agents comprise, inter alia, nucleic acid molecules as well as antisense nucleic acid molecules which encode Pax proteins or specifically inhibit the expression of Pax genes, respectively. Furthermore, U.S. Pat. No. 5,747,250 relates to therapeutic or diagnostic agents containing at least one Pax protein, selected from the group consisting of Pax1, Pax2, Pax3, Pax4, Pax5, Pax6, Pax7, Pax8, HuP1, HuP2, prd, BSH4, BSH9, Pox neuro and Pox meso. U.S. Pat. No. 5,747,250 employs said genes in tumor diagnosis and/or therapy and does not provide for any means or methods for the amelioration of renal diseases nor provides for specific transcription factors involved in renal regeneration.

Thus, the technical problem of the present invention is to provide for means and methods useful for the protection from and/or the amelioration of renal diseases, in particular to provide for means and methods to influence physiological processes that lead to a decrease of renal function.

The solution of this technical problem is achieved by providing the embodiments characterized in the claims.

Accordingly, the present invention relates to a method for treating, delaying and/or preventing renal dysfunction/failure in a mammal comprising administering a therapeutically effective amount of a substance capable of inducing and/or enhancing Pax2 expression. Preferably, the mammal in this and the following embodiments is a human.

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e.

arresting its development and/or progress; or (c) relieving the disease, i.e. causing regression of the disease.

Furthermore, it is envisaged that the above mentioned method for treating, delaying and/or preventing renal diseases comprises methods like tissue engineering. Tissue engineering is the process by which a new tissue is created artificially in vivo or in vitro. In practice, tissue engineering is the process by which vital tissue is created with organ-specific characteristics and functions such as mechanical integrity, biostability, microstructure and biochemical activity. Tissue engineering encompasses all biological and molecular aspects which are necessary for tissue formation which include for instance cell differentiation and proliferation, cell-cell and cell subtrate interactions and their collective organisation into an integral structure-to-organ. In the future reconstructive organ surgery that uses cell/tissue or whole organ transplantation technologies will be replaced by regeneration organ surgery, as a new medical discipline, that uses devices to induce reparative histogenesis processes directly from the cells of the host organ or by introducing stem cells (Woerly (2000) XI; Tissue engineering, Introduction, p. 1-15).

Tissue morphogenesis in postnatal life and embryonic development are similarly regulated by few and highly conserved families of morphogens (Reddi (1997), Cytokine Growth Factors Rev. 8: 11-20; Ripamonti (1998), Plat. Reconstr. Surg. 101: 227-239) which are distributed to many tissues and organs. So it is obvious to suggest that a plurality of morphogens are required to promote synchronously and synergistically the cascade of pattern formation or morphogenesis or if not to singly initiate this process. Future molecular therapeutics for tissue morphogenesis/organ regeneration of the adult organism will require pattern of protein expression and co-localization of morphogens, recapitulating events which occur during the normal course of embryonic development. The concept that induction of highly specialized adult tissue in postnatal life shares identical mechanisms with embryonic development has suggested that the "memory" of developmental events in embryo can be redeployed postnatally by the application of synergistic morphogen combinations (Ripamonti (1997), J. Bone Min. Res. 12: 1584-1595).

Therefore the future will bring a therapeutic "mosaicism" in tissue engineering, and require extensive testing of doses and ratios of recombinant morphogen combinations or their stimulators in clinical context.

As documented in the appended examples it has surprisingly been found that the expression of Pax2 is implied and necessary in the amelioration of renal dysfunction/failure. Furthermore, it could most surprisingly be demonstrated that, after induction of an artificial renal dysfunction/failure in experimental animals, blockage of Pax2 by antisense approaches lead to the death of said animals. Therefore, Pax2, whether stabilized in a physiological context, whether administered as a protein (or as (a) functional fragment(s) therof), as a nucleic acid molecule encoding Pax2 or expressed in vivo or in vitro by a substance capable of inducing and/or enhancing can be employed as a medicament for the treatment of renal dysfunction/failure, in particular for the treatment of acute tubular necrosis. Hence, the present invention relates to substances/drugs which are capable of in vivo and in vitro inducing and/or enhancing the Pax2 protein level in a cell, preferably in a kidney cell, even more preferably in a cell of the proximal tubuli. Said induction and/or enhancement also comprises any in vivo stimulation of Pax2 expression by said substances. Considering the fact that Pax2 is a transcription factor, any Pax2 protein or any functional fragment thereof can be considered as a substance which induces or enhances Pax2 expression since, via feed-back mechanisms, said functional Pax2 may lead to said in vivo stimulation of Pax2 protein in a cell. In connection with the present invention, the term "functional fragment(s)" of the Pax2 protein denotes fragments that retain or essentially retain the capability to process the above described therapeutic or prophylative effect. Such functional fragments comprise, but are not limited to, fragments which are responsible for its nuclear localization, its transacting potential and/or its DNA recognition capacities. Such functional fragments can be, inter alia, deduced by homology screenings with other transcription factors, for example by comparison with other homeobox genes.

Furthermore, the present invention relates to a method for treating, delaying and/or preventing renal dysfunction/failure wherein said induction and/or enhancement of Pax2 expression takes place on the transcription and/or the translation level. In accordance with the present invention, said induction and/or enhancement may lead to an elevated level of mRNA coding for Pax2 protein and/or an elevated level of functional Pax2 protein and/or (a) fragment(s) thereof.

In a preferred embodiment said induction and/or enhancement is a transient induction and/or transient enhancement of Pax2 expression.

In another preferred embodiment, the method of the invention relates to a method for treating, delaying and/or preventing renal dysfunction/failure, wherein said renal dysfunction/failure is acute or chronic renal failure. In a preferred embodiment, said acute renal failure is acute tubular necrosis.

Furthermore, the present invention relates, in an even more preferred embodiment to a method for treating, delaying and/or preventing renal dysfunction/failure wherein said substance capable of inducing and/or enhancing Pax2 expression is selected from the group consisting of a nucleic acid molecule encoding Pax2 protein, a Pax2 protein or (a) functional fragment(s) thereof, a growth factor, a cytokine, lithium, LIF (leukemia inhibiting factor) osteopontin, an apoptotic protein and STAT3 (signal transduction and activator of transcription).

Pax2, being a transcription factor, is not only involved in the transcription of genes implicated in the development of multicellular differentiated tissue but may also be involved in feed-back regulation mechanisms. Therefore, a substance capable of inducing and/or enhancing Pax2 expression may also be a nucleic acid molecule encoding Pax2 and thereby elevating the Pax2 protein level in a cell or may be a Pax2 protein (or (a) functional fragment(s) thereof) itself which leads, via said feed-back mechanism, to increased Pax2 levels in a cell and thus the desired pharmaceutical and/or therapeutical effect. The nucleic acid sequence and the protein sequence of Pax2 is well known in the art (Dressier (1990), Development 109, 787-795; Sanyanusin (1996), Genomics 35, 258-261; Eccles (1992), Cell Growth Differ. 3, 279-289; Ward (1994), Cell Growth Differ. 5, 1015-1021; Stapleton (1993), Nat. Genet. 3, 292-298; Tavassoli (1997), Hum. Genet. 101, 371-375) and can be obtained be easily obtained by database screens, as described herein below.

The term "nucleic acid molecule" in accordance with the present invention comprises coding and, wherever applicable, non-coding sequences (like promoters, enhancers etc.). In accordance with the present invention, the term "nucleic acid molecule" comprises also any feasible derivative of a nucleic acid to which a nucleic acid probe may hybridize. Said nucleic acid probe itself may be a derivative of a nucleic acid molecule capable of hybridizing to said nucleic acid molecule or said derivative thereof. The term "nucleic acid molecule" further comprises peptide nucleic acids (PNAs) containing DNA analogs with amide backbone linkages (Nielsen, Science 254 (1991), 1497-1500). The term "nucleic acid molecule" which encodes a Pax2 protein (and/or a fragment thereof) in connection with the present invention, is defined either by (a) the specific nucleic acid sequences encoding the said Pax2 protein (and/or a fragment thereof) or (b) by nucleic acid sequences hybridizing under stringent conditions to the complementary strand of the nucleotide sequences of (a) and encoding a Pax2 protein and/or a fragment thereof deviating from the nucleic acid of (a) by one or more nucleotide substitutions, deletions, additions or inversions and wherein the nucleotide sequence shows at least 40%, preferably at least 50%, more preferably at least 60% identity with the nucleotide sequence of said encoded Pax2 protein having an amino acid sequence as defined in the art and described herein above. The wild-type nucleic acid sequences encoding Pax2 protein (or (a) fragment(s) thereof are easily obtainable or deducible from (Dressler (1990), Development 109, 787-795; Sanyanusin (1996), Genomics 35, 258-261; Eccles (1992), Cell Growth Differ. 3, 279-289; Ward (1994), Cell Growth Differ. 5, 1015-1021; Stapleton (1993), Nat. Genet. 3, 292-298; Tavassoli (1997), Hum. Genet. 101, 371-375).

The term "Pax2 protein" means, in accordance with the present invention, a peptide, a protein, or a (poly)peptide which encompasses amino acid chains of any length functioning as a Pax2 protein or a fragment thereof wherein the amino acid residues are linked by covalent peptide bonds. However, peptidomimetics of such proteins/(poly)peptides wherein amino acid(s) and/or peptide bond(s) have been replaced by functional analogs are also encompassed by the invention.

Said growth factor capable of inducing and/or enhancing Pax2 expression is selected from the group consisting of FGF2, bFGF, TGF-α, TGF-β, FGF9, oncostatin M, PDGF-α, EGF, IGF-I (insulin like growth factor-I) and HGF/SF(hepatocyte growth factor/scatter factor) GDNF, osteopontin, Wnt-1, Wnt-4 and BMP7.

FGF2, bFGF, EGF, IGF-I, HGF/SF have been shown to influence the mesenchyme to epithelium conversion or the tubulogenesis process directly (stimulate) or indirectly via expression of the receptors for the signaling molecules (e.g. met receptor expression in the ureter as ligand for HGF/SF which is expressed in the mesenchyme) in the epithelium compartment of the nearby developing ureter. Addition of FGF9 (Barasch (1999), Cell 99, 377-386) lead to epithelialization of mouse mesenchyme. Oncostatin M induced epithelialization of rat mesenchyme in vitro (Barasch (1999), loc. cit.). TGFα was necessary for the action of LIF, which lead to Pax2 expression in vitro in metanephric mesenchyme (Barasch (1999), loc. cit.).

TGF-β was shown to participate in renal regeneration after postischemic injury by restoring extracellular matrix homeostasis in proximal tubular basement membrane (Basile (1998b), Am. J. Physiol. 275: F894-F903). Specifically in the S3 (straight) segment of the proximal tubule regeneration occurs following ischemic injury (Basile (1998a), Miner. Electrolyte Metab. 24: 144-148). Earlier, same investigators already observed (Basile (1996), Am. J. Physiol. 270: F500-F509) that TGF-β1 mRNA were elevated significantly at 12 h postinjury (1.5 fold vs. sham operated controls), and by 24 h postinjury were elevated by 3.6 fold. Levels remained elevated for 14 days following ischemia, but were no longer elevated at 28 days postinjury. Immunohistochemical staining localized active TGF-β to the lumen of proximal tubules in control animals and in desquamated and regenerating tubular epithelial cells following ischemia. TGFβ bioactivity may, after renal injury, be induced by the upregulated Pax2 protein for enhancing tubular regeneration of matrix homeostasis.

GDNF (glial cell-derived neurotrophic factor), a distant relative of TGF-β, was also shown to be critical for proper kidney development (Pichel (1996), Nature 382: 73-76; Sanchez (1996), Nature 382, 70-73; Moore (1996), Nature 382: 76-79; Vega (1996), PNAS 93: 10657-10661). GDNF causes tyrosine phosphorylation of RET after binding to an accessory receptor, GDNFRα (Jing (1996), Cell 85: 1113-1124; Treanor (1996), Nature 382:80-83). Renal mesenchymal cells express GDNF (Hellmich (1996), Mech. Devel. 54: 95-105). Homozygous null mutations for GDNF in mice do not develop kidneys. Heterozygotes for the GDNF mutation have kidney malformations. GDNF binds the receptor tyrosine kinase RET with a dissociation constant of 8 nM, and 125I-labeled GDNF can be co-immunoprecipitated with anti-RET antibodies.

Interestingly, exogenous supplementation of the mesenchyme derived factor GDNF stimulated both branching of the ureter and also supported proliferation of embryonic kidneys in organ culture (Vega (1996), PNAS 93: 10657-10661). Moreover, the activation of the RET pathway resulted in increased cell motility, dissociation of cell adhesion, and the migration towards a localized source of GDNF (Tang (1998), J. Cell Biol. 142: 1337-1345) in an in vitro assay of MDCK cells, a dog kidney epithelial cell line of tubular origin. Regeneration and the stimulation of regenerative events in the adult kidney also requires cell migration, cell motility and the dissociation of cell adhesion in response to positional cues like in embryonic kidney development. Therefore GDNF can be considered as an important cofactor for Pax2 in order to reconstitute a damaged renal tubular epithelium after injury.

Wnt genes encode glycoproteins thought to act as secreted signalling factors. Wnt-1-transfected fibroblasts induce nephron formation during coculture with isolated renal mesenchyme (Herzlinger (1994), Dev. Biol. 166, 815-818). Wnt-1 has been shown to be capable of initiating condensation and tubulogenesis in uninduced mesenchyme. Wnt-4 is upregulated in renal mesenchymal cells as they differentiate into nephrons (Stark (1994), Nature 372, 679-683). Null mutation mice for Wnt-4 manifest with renal aplasia, even when metanephroi of those embryos are induced. The mesenchyme of those animals appears to be "frozen" in an undifferentiated state. Pax2 upregulation in adult kidneys of acute renal failure therefore is considered, in accordance with this invention to need the coactivation of Wnt-4 to sufficiently enhance and terminate further differentiation of injured tubulus epithelium.

Bone morphogenetic proteins (BMPs) are members of the TGFβ-superfamily and transduce growth signals through type I and II receptor serine/threonine kinases. BMP7 is expressed by the ureter bud branches during early kidney development and is also upregulated in primitive nephrons (Dudley (1995), Genes Dev. 9: 2795-2807; Luo (1995), Genes Dev. 9: 2808-2820).

Interestingly Lithiumchloride has been shown to promote induction of isolated mesenchyme (Davies (1995), Dev. Biol. 167, 50-60); Lithium functions also as inhibitor for glycogen synthase 3-kinase (GSK-3 beta) and thus activates the Wnt signalling pathway (Klein (1996), PNAS 93, 8455-8459). Recent data from Godin (1998; Development 125, 3473-3482) suggest that BMP7 expression in the mesenchyme is activated upon LiCl treatment, suggesting that activation of BMP7 lies downstream of a Wnt signal. Treatment of whole kidneys with sodium chlorate—which disrupts proteoglycan synthesis—results in the loss of BMP7 expression in the mesenchyme whereas expression in the epithelial components of the kidney are unaffected (Godin (1998) Development 125, 3473-3482). Therefore BMP7 expression in the epithelial components of the kidney is not dependent on cell-cell or cell-extracellular matrix (ECM) interactions with the metanephric mesenchyme. Recent data (Dudley (1999), Genes Dev. 13: 1601-1613) have shown that BMP7 in conjunction with FGF2 promotes growth and maintains competence of the renal mesenchyme in vitro, which by BMP7 action alone is not achievable. Even when FGF2 and BMP7 alone and in combination (Dudley (1999), Genes Dev. 13: 1601-1613) are shown to inhibit tubulogenesis both factors may be necessary fostering regeneration after adult renal failure. This suggestion is supported by data from Vukicevic (1998, J. Clin. Invest. 102: 202-214) which have shown that recombinant BMP7 was able to ameliorate treatment of acute renal failure. Rats given BMP7 10 min. before or 1 h or 16 h after ischemia demonstrated a) a smaller infarction area and cell necrosis as well as decreases in the number of plugged tubules. BMP7 action also resulted in reduced programmed cell death during recovery. Collectively, those data suggested that BMP7 (synonymous OP-1) prevents the loss of kidney function associated with ischemic injury/reperfusion and provides together with other factors a basis for the treatment of acute renal failure. Recently a membrane bound, specific, high-affinity receptor for BMP7 (BMP Type II receptor) was postulated (Bosukunda (2000), Kidney Int. 58: 1902-1911) with a relative molecular mass of about 100 kD. In vivo and in vitro data suggest that the cellular targets for BMP7 beyond glomeruli and collecting duct are convoluted kidney tubule. BMP7 is therefore supposed to act directly on injured tubule cells modifying specifically their response to Pax2; similar to its action on neural cells, where their response to sonic hedgehog (SHH) is influenced so that they differentiate into rostral diencephalic ventral midline cells rather than floor plate cells (Dale (1997), Cell 90: 257-269).

Cytokines capable of inducing and/or enhancing Pax2 expression may be selected from the group consisting of Il-6, TNF-α and Il-6 type cytokines.

Barasch (1999), loc. cit. demonstrated that Il-6 type cytokines acted like LIF (produced by budding ureter cells which acted on epithelial precursors which expressed Pax2 and Wnt4) leading to Pax2 expression in metanephric mesenchymal cells.

As mentioned herein above, lithium can be considered as a substance capable of inducing and/or enhancing Pax2 expression for the treatment, for delaying and/or preventing renal dysfunction/failure in a mammal. Lithium salt has been proposed by Davies and Garrod (1995, Dev. Biol. 167, 50-60) as an ion capable of stimulating Pax expression. Furthermore, in Davies and Garrod (1995), loc. cit. and Davies and Bard (1996; Exp. Nephrol 4, 77-85), lithium has been shown to induce aggregation of isolated mesenchymal cells in vitro and also lead to Pax2 expression in those aggregates already 4 hours after lithium was administered. It is also known that lithium is capable to use the promiscuous transporter system in the adult kidney tubule system which usually transports sodium.

Furthermore, LIF (leukemia inhibiting factor) can be employed in the methods, as well as in the use (see herein below) of the present invention. LIF (leukemia inhibitory factor) has been shown to be secreted from budding ureter cells at the beginning of metanephric development (Barasch (1999), loc. cit.). LIF acted on epithelial precursors which expressed Pax2 and Wnt4. Other Il-6 type cytokines acted like LIF. LIF triggers epithelialization, tubulogenesis and nephrogenesis in isolated metanephric mesenchymes. Thus LIF may also be suitable for acting in the adult organism to enhance or initiate Pax2 expression in proximal tubuli in acute renal failure. LIF action in vitro requires pretreatment with mesenchymal growth factors as FGF2, TGFα or FGF9 (Barasch (1999), loc. cit.). To examine whether LIF acts on epithelial precursors (Pax2, Wnt4 expressing cells) metanephric mesenchymes were cultured with FGF2 and monitored for the activation of STAT3 (signal transduction and activator of transcription)—a target of gp130 activation—only 1 h after exposure to LIF, phosphorylated STAT3 was prominent in the nuclei of these cells, suggesting that the cytokine can directly activate second messenger signaling in epithelial precursors.

Osteopontin (Eta1) is a negatively charged phosphoprotein and possesses an arginine-glycine-aspartic (RGD) acid-serine cell attachment sequence recognized by several integrins and has been shown in vitro to serve as an attachment substrate to several cell types via integrins and CD44, the cell-surface proteoglycan hyaluronic acid receptor (Weber (1996), Science 271: 509-512). Pretreatment of rats with insulin-like growth factor I (IGF-I) ameliorates the course of acute ischemic renal injury by inducing osteopontin (Padanilam (1996), Endocrinology 137, 2133-2140). IGF-I pretreatment resulted in enhanced levels of osteopontin mRNA 12 h, 1 day, and 5 days postinjury. Five days post, injury, osteopontin peptide and mRNA were detected in regenerating proximal tubules. Osteopontin probably serves to promote tissue regeneration and tissue remodelling within 1 day after acute ischemic injury of the kidney and may therefore co-act together with Pax2. Therefore IGF-I enhanced expression of osteopontin at an earlier time postischemia may ameliorate the course of injury via concerted action with Pax2.

As mentioned herein above, substances capable of inducing and/or enhancing Pax2 expression which comprise apoptotic proteins. In a particular preferred embodiment said apoptotic protein is CHOP, bax or bcl-2.

Intracellular molecules like BCL2 have a major impact on metanephric growth by affecting kidney cell survival (Sorensen (1995), Am. J. Physiol. 268: 73-81). Bax and bcl-2 in adult kidneys are known as regulators of regeneration (Basile (1997), Am. J. Physiol. 272: F640-F647). After renal injury, the expression of bcl-2 mRNA was markedly enhanced (2.1-fold within 24 h of injury) in regenerating proximal tubule cells relining the basement membrane. Same pattern was shown for protein of bcl-2. Levels remained elevated for 3 days and returned to baseline by day 5 postischemia. Bax mRNA and bax protein were colocalized to regenerating proximal tubules postischemia. It can be concluded that the expressions of bcl-2 and bax in kidney are enhanced in a predictable pattern following acute renal injury. So it can be suggested that these regulators of apoptosis play key roles in the process of repair of the damaged proximal tubule postischemia. Gobe and coworkers also demonstrated that after ischemic acute renal failure in rats bcl-2 was expressed in advance of known regenerative growth factors like IGF-1 and EGF in proximal and distal tubules (Gobe (2000), J. Am. Soc. Nephrol. 11: 454-467). It is suggested that the distal tubule is adaptive resistant to ischemic injury via promotion of survival by anti-apoptotic bcl genes, and its survival allows expression of growth factors critical not only in the maintenance and regeneration of its own cell population (autocrine), but also to the adjacent ischemia-sensitive proximal tubular cell. The effective regeneration process of proximal tubular epithelium after acute renal failure is therefore considered, in accordance with this invention to depend on prolonged and continuous expression of bcl-2 as a downstream factor of Pax2 necessary for anti-apoptotic survival of critically injured epithelium.

The therapeutically effective amount of a substance capable of inducing and/or enhancing Pax2 expression may be in a composition or in form of a composition. Said composition may be in solid, liquid or gaseous form and may be, inter alia, in the form of (a) powder(s), (a) tablet(s), (a) solution(s) or (an) aerosol(s). Therefore, the present invention relates to a method for treating, delaying and/or preventing renal dysfunction/failure, wherein substances are employed as defined herein above which may be in form of a pharmaceutical composition, optionally further comprising an acceptable carrier and/or diluent and/or excipient. The pharmaceutical composition of the present invention may be particularly useful in preventing, delaying and/or treating pathological renal disorders in humans or animals. Said pathological disorders comprise, but are not limited to, acute and chronic renal dysfunction/failure. These disorders comprise, inter alia, acute tubular necrosis (of prerenal/hemodynamic and renal origin) as well as acute tubular necrosis after renal transplantation, drug associated acute renal failure and toxic acute renal failure. Chronic renal failure comprise all disorders of renal insufficency, i.e. after glomerulonephritis of different origin or chronic renal failure of patients after renal transplantation.

As stated herein above, the pharmaceutical composition may also be used for prophylactic purposes.

Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. However, it is also envisaged that the pharmaceutical compostions are directly applied to the nervous tissue. The dosage regimen will be determined by the attending physician or veterinarian and clinical factors. As is well known in the medical arts, dosages for any one patient depends upon many factors, including the patient's size, body surface area, body weight, renal function, general health, age, sex, the particular compound to be administered, time and route of administration, and other drugs being administered concurrently. Pharmaceutically active matter may be present, inter alia, in amounts between 1 μg and 5 g per dose; however, doses below or above this exemplary range are envisioned, especially considering the aforementioned factors. If the regimen is a continuous infusion, it should also be in the range of 1 μg to 10 mg units per kilogram of body weight per minute, respectively. The administration of nucleic acid molecules encoding Pax2 protein (and/or a fragment thereof) amounts of 1 μg to 5 mg/kg body weight per dose are envisaged. Vectors, including expression and/or gene targeting or gene transfer vectors (like vival vectors) may be administered in doses of 1 μg to 5 mg/kg body weight. However, doses above and below the here given values are also envisaged. Progress can be monitored by periodic assessment. The compositions/substances which induce and/or enhance Pax2 expression may be administered locally or systemically. Administration will generally be parenterally, e.g., intravenously. The compositions/substances which induce and/or enhance Pax2 expression may also be administered directly to the target site, e.g., by biolistic delivery to an internal or external target site like the kidney or by catheter to a site in an artery or may be directly delivered to renal and/or mesenchymal tissue. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Furthermore, the pharmaceutical composition of the invention may comprise further agents, depending on the intended use of the pharmaceutical composition. Such agents may be drugs acting on the excretory/secretory system of the kidney or the urinary tract as well as on the proximal and/or distal tubular function, the glomerular function and/or the function of the collecting duct system. Furthermore said pharmaceutical composition may additionally comprise drugs and compounds which may influence glomerular filtration. Further drugs acting on the excretory system or the urinary tract during renal failure comprise, but are not limited to loop diuretics (e.g. furosemide) or antihypertensive drugs like calcium antagonists (e.g. nifedipine) or angiotensin-converting-enzyme-inhibitors (e.g. ramipril or lisinopril).

In a particular preferred embodiment, the nucleic acid molecule encoding Pax2 protein (and/or (a) functional fragment(s) thereof) and capable of inducing and/or enhancing Pax2 expression is part of a vector. Therefore, the present invention relates in another embodiment to a method of treatment wherein the nucleic acid molecule encoding Pax2 protein is comprised in a vector. Such a vector may be, e.g., a plasmid, cosmid, virus, bacteriophage or another vector used, e.g. in therapeutic uses and/or in vitro/in vivo tissue engineering. Said vector may comprise further genes such as marker genes which allow for the selection of said vector in a suitable host cell and under suitable conditions or which allows the monitoring of correct expression in cells and/or tissues.

Furthermore, the vectors may, in addition to the nucleic acid sequences encoding Pax2 protein, comprise expression control elements, allowing proper expression of the coding regions in suitable cells, tissues and/or organs. Such control elements are known to the artisan and may include a promoter, translation initiation codon, translation and insertion site for introducing an insert into the vector. Preferably, the nucleic acid molecule encoding Pax2 protein (and/or a fragment thereof) is operatively linked to said expression control sequences allowing expression in eukaryotic or prokaryotic cells. Particularly preferred are in this context control sequences which allow for correct expression in renal cells and/or cells derived from kidney tissue and/or in undifferentiated, pluripotent, mesenchymal cells. Particularly preferred are therefore control sequences which allow correct expression in metanephric cells, like the LTR sequences of the expression plasmid pCMV-Pax2b (Lechner and Dressler (1996), J. Biol. Chem. 271, 21088-21093) which activate and drive transcription of the Pax2 gene in mesenchymal cells. Within the COOH terminus of Pax2, amino acids 279-373 are essential for transactivation. However this region alone is insufficient for full transctivation when fused to the paired domain alone or to a heterologous DNA binding domain. Mutation or deletion of the conserved octapeptide sequence results in increased transactivation by Pax proteins. The octapeptide-mediated repression is also seen with a heterologous cintext using the GAL4 DNA binding domain. Thus transactivation by Pax2 relies upon several regions within the COOH terminus and is down-modulated by the octapeptide element.

Another example of cell specific transactivation of Pax2 includes co-transfection experiments with Pax2 expression constructs in CHO-K1 cells (McConnell (1997), Oncogene 14, 2689-2700). PAX2 transactivated the WT1 promoter up to 35 fold in CHO-K1 cells, and four to sevenfold in 293 cells. Two regions of the WT1 promoter were required in the same promoter construct for efficient transactivation by PAX2 in CHO-K1 cells, and purified recombinant PAX2 protein was found to bind to two sites in the WT1 (McConnell (1997), loc. cit.) promoter, at −205/230 and +377/+402. Removal of WT1 promoter sequences containing the −205/−230, or +377/+402 binding sites abolished transactivation of the WT1 promoter by PAX2 in CHO-K1 cells, and had a differential effect on transactivation of the WT1 promoter in 293 cells, depending on the PAX2 isoform used. A fragment containing the −205/−230 site alone could be transactivated by PAX2.

Control elements ensuring expression in eukaryotic cells are well known to those skilled in the art. As mentioned above, they usually comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions. Possible regulatory elements permitting expression in for example mammalian host cells comprise the CMV-HSV thymidine kinase promoter, SV40, RSV-promoter (Rous sarcomea virus), human elongation factor 1α-promoter, CMV enhancer, CaM-kinase promoter or SV40-enhancer. For the expression for example in kidney/renal tissue and/or cells derived therefrom, several regulatory sequences are well known in the art, like the CMV promoter of CMV-CAT (as described in Foecking (1986), Gene 45, 101-105; Furth (1991), Nuc. Acids Res. 19, 6205-6208), which specifically expresses Pax2 in embryonic kidneys (Dressler (1993), Nature 362, 65-67). Beside elements which are responsible for the initiation of transcription such regulatory elements may also comprise transcription termination signals, such as SV40-poly-A site or the tk-poly-A site, downstream of the polynucleotide. In this context, suitable expression vectors are known in the art such as Okayama-Berg cDNA expression vector pcDV1 (Pharmacia), pRc/CMV, pcDNA1, pcDNA3 (In-Vitrogene, as used, inter alia in the appended examples), pSPORT1 (GIBCO BRL) or pGEMHE (Promega). Beside the nucleic acid molecules encoding Pax2 protein the vector may further comprise nucleic acid sequences encoding for secretion signals. Such sequences are well known to the person skilled in the art. Furthermore, depending on the expression system used leader sequences capable of directing the protein/(poly)peptide to a cellular compartment may be added to the coding sequence of the nucleic acid molecules of the invention and are well known in the art. The leader sequence(s) is (are) assembled in appropriate phase with translation, initiation and termination sequences, and preferably, a leader sequence capable of directing secretion of translated protein, or a part thereof, into, inter alia, the nucleus. Optionally, the heterologous sequence can encode a fusion protein including an C- or N-terminal identification peptide imparting desired characteristics, e.g., stabilization or simplified purification of expressed recombinant product. Of course, the vector can also comprise regulatory regions from pathogenic organisms.

Furthermore, said vector may also be, besides an expression vector, a gene transfer and/or gene targeting vector. Gene therapy, which is based on introducing therapeutic genes into cells by ex-vivo or in-vivo techniques is one of the most important applications of gene transfer. Suitable vectors, vector systems and methods for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813, Isner, Lancet 348 (1996), 370-374; Muhlhauser, Circ. Res. 77 (1995), 1077-1086; Wang, Nature Medicine 2 (1996), 714-716; WO 94/29469; WO 97/00957, Schaper, Current Opinion in Biotechnology 7 (1996), 635-640 [bitte ergänzen Sie relevante Literaten, die gentherapeutische Ansätze in der Niere beschreiben.] or Verma, Nature 389 (1997), 239-242 and references cited therein. As shown in the appended examples, a suitable vector for expression of a nucleic acid molecule encoding Pax2 protein is the retroviral vector pMMuLV-SVTK-NEO, as described in Rubenstein (1984), PNAS USA 81, 7137-7140.

Transfer of genetic information into the adult kidney was recently successfully mediated using the adeno associated virus (AAV) system (Lipkowitz (1999), J. Am. Soc. Nephrol. 10: 1908-1915). AAV, which is a defective virus of the parvovirus family, has a number of properties attractive for renal gene delivery: 1) recombinant AAV contains no viral genes; 2) expression of genes delivered by these vectors does not activate cell-mediated immunity; 3) the virus is able to transduce nondividing as well as dividing cells; and 4) both wild type and recombinant AAV integrate into the host chromosome resulting in long term gene expression. The authors were able to demonstrate that AAV can deliver reporter genes to human proximal tubule, mesangial, thick ascending limb, collecting tubule, and renal cell carcinoma cells in primary culture. AAV delivered in vivo by intraparenchymal injection results in at least 3 months of reporter gene expression in tubular epithelial cells. Since AAV preferentially transduce cells in S-phase of the cell cycle (Russel (1994), PNAS 91: 8915-8919) that viral feature can be optimal utilized for the treatment of acute renal failure/regeneration where many proximal tubular cells again enter the cell cycle and go through S-phase in order to regenerate. One major drawback of AAV vectors for gene therapy has been its limitation to relative small disease genes (packaging size of 5 kb); this problem has been solved now via trans-splicing between two independent vectors coadministered to the same tissue (Yan (2000), PNAS 97: 6716-6721). So it is possible to apply AAV technology for Pax2 related recovery in acute renal failure.

Bosch (1993; Exp. Nephrol. 1: 49-54) tried to transfer genes via a retroviral vector system (Psi2 BAG) into normal kidney and discovered that the very low mitotic index of the kidney was responsible for their lack of success. However, if the tubular epithelial cells were damaged using folic acid, they subsequently proliferated and gene transfer into regenerating tubular epithelial cells was successful demonstrated by using beta-galactosidase activity as a marker.

Specific transfection of proximal tubular cells is critical for treatment of acute renal failure via gene therapy. Therefore exact controlling of transgene destination is the ultimate prerequisite for optimal transgene expression in injured tissue. Such specific and successful cell targeting with expression in tubular cells was recently done using polyplexes which were injected into the renal artery (Poglieni (2000), Gene Ther. 7: 279-285). Size measurements by laser light scattering demonstrated that the mean diameter of polyplexes (93 nm) was smaller than that of lipoplexes (160 nm; containing the cationic lipid DOTAP), which before failed to specifically target tubular cells—since glomerular filtration barrier could not be passed. The size of the transfecting particles is therefore a key parameter and relevant for optimal expression in tubular cells. Exogeneous transfection of Pax2 into injured tubular epithelial cells in order to support regeneration should therefore include the application of polyplexes as vehicles for Pax2 protein/DNA complexes.

For liposome mediated gene transfer in the kidney see Lai (1997; Gene Ther. 4: 426-431). The authors obtained a transient transfer into tubules. Since regeneration mechanisms and the proteins involved in that after acute renal failure are of transient nature, a transient transfer of genetic material (Pax2) is deliberately the best choice to support regeneration.

For ex vivo gene transfer approaches into the kidney see Kelley (1999; Am. J. Physiol. 276: F1-F9). In that experimental setup renal parenchymal cells were used as vehicles to deliver molecules to a prescribed site in the kidney. Because these renal parenchymal cells are genetically modified to generate a selected molecule and these cells are then re-introduced into the kidney with the intention of delivering the selected molecule, authors use the term "carrier" cells.

One might select (biopsy) and use tubular epithelial cells from a person who suffers from acute renal failure, and modify those cells in the described way to determine the impact of delivery of Pax2 on thwarting renal injury with "carrier" cells.

For an actual general overview regarding different kidney-targeting gene transfer methods including viral vectors—retroviral, adenoviral—and gene delivery methods including hemagglutinating virus of Japan (HVJ) liposomes, cationic liposomes, and future applications for kidney diseases see Kelley (1999; Am. J. Physiol. 276: F1-F9).

Searching for tissue specific promoters for future kidney targeted gene therapy Lai (1998; Life Sci. 63: 121-126) demonstrated that the human carbonic anhydrase II (CAI II) 5' sequence of proximal 1.3 kb contains strong promoter sequences for renal tubular cells.

By studying organ-selctive targeting based on in vivo screening of random peptide sequences, authors (Pasqualini (1996), Nature 380: 364-366) detected peptides capable of mediating selective localization of phage to brain and kidney blood vessels. Recently the same laboratory (Trepel (2000), Hum. Gene Ther. 11: 1971-1981) further improved technique lead to the development of molecular adaptors to target adenoviral gene therapy vectors to selective vascular "addresses". The peptides isolated by this approach bind to receptors expressed in vascular endothelia. The adaptor design consists of an organhoming peptide conjugated to an adenovirus-binding moiety. The authors isolated and characterized several monoclonal antibodies that bind to adenovirus type 5 (Ad5). Two of those antibodies neutralized Ad5 infection. Authors linked the Fab fragments of one of these antibodies to a synthetic lung-homing peptide (GFE-1) and tested the ability of the resulting bispecific conjugate to retarget Ad5. Cells expressing the receptor for the lung-homing peptide and are resistant to Ad5 infection were sensitised to recombinant Ad5 vectors in the presence of the Fab-GFE adaptor. The findings indicate that selective gene therapy delivery may be developed on the basis of this vascular targeting technology for different organs and tissues. Peptide sequences and adaptors may in the future efficiently help govern cells, drugs and genes into selected tissues.

The nucleic acid molecules and vectors as described herein above may be designed for direct introduction or for introduction via liposomes, or viral vectors (e.g. adenoviral, retroviral) into the cell. Additionally, baculoviral systems or systems based on vaccinia virus, adeno associated virus (AAV) or Semliki Forest Virus can be used as eukaryotic expression system for the nucleic acid molecules encoding Pax2 protein. In addition to recombinant production the Pax2 protein and/or fragments of the Pax2 protein, fusion proteins comprising Pax2 amino acid sequences may be produced by direct peptide synthesis using solid-phase techniques (cf Stewart et al. (1969) Solid Phase Peptide Synthesis, W H Freeman Co, San Francisco; Merrifield, J. Am. Chem. Soc. 85 (1963), 2149-2154). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments may be chemically synthesized separately and combined using chemical methods to produce the full length molecule. As pointed out herein above, the present invention, therefore, relates in a preferred embodiment to a method of the invention wherein said vector comprising a nucleic acid molecule encoding Pax2 is an expression vector and/or a gene targeting vector or a gene transfer vector. Particularly preferred are, as mentioned herein above, said vector comprises an expression control sequence. In a particular preferred embodiment the method of the invention relates to a method wherein said induction and/or enhancement of Pax2 expression takes place in cells of the proximal tubuli of the kidney.

In a further particular preferred embodiment, the method of the present invention relates to a therapeutic method as described herein above wherein therapeutically effective amount of a substance is with range of 1 µg to 5 g. However, concentrations above or below this limits are also envisaged and depend on factors as described herein above. Since the kidney which has an impaired function is particularly sensitive to any potentially toxic insult, substances capable of inducing and/or enhancing Pax2 expression should be administered in concentrations which do not cause any additional histological, physiological and/or functional problem.

Furthermore, the present invention relates to the use of an effective dose of a substance capable of inducing and/or enhancing Pax2 expression in a mammal for the preparation of a pharmaceutical composition for treating, preventing or delaying a renal dysfunction/failure in a mammal. In a preferred embodiment, said renal dysfunction/failure is acute or chronic renal failure, and in an even more preferred embodiment said acute renal failure is acute tubular necrosis.

The present invention relates, in a yet even more preferred embodiment to the use of the invention wherein said substance capable of inducing and/or enhancing Pax2 expression is selected from the group consisting of a nucleic acid molecule encoding Pax2 protein, a Pax2 protein, a growth factor, a cytokine, lithium, LIF (leukemia inhibitory factor), osteopontin, an apoptotic protein and STAT3 (signal transduction and activator of transcription).

Particular preferred growth factors are FGF2, bFGF, FGF9, TGF-α, TGF-β, oncostatin M, PDGF-α, EGF, IGF-I (insulin like growth factor-I) and HGF/SF (hepatocyte growth factor/scatter factor), particular preferred cytokines are IL-6, IL-6 type cytokines, TNF-α, GDNF, Wnt-1, Wnt-4 and BMP7.

In a yet more preferred embodiment, the present invention relates to the use of the invention wherein said nucleic acid molecule encoding Pax2 is comprised in a vector. Said vector may be an expression vector and/or a gene targeting vector or a gene transfer vector. Said expression vector and/or gene targeting vector or gene transfer vector may further comprise an expression control sequence.

Additionally, the present invention relates to the use of the invention wherein said effective dose of a substance capable of inducing and/or enhancing Pax2 expression is in the range of 1 µg to 5 g. Preferably in a range of 1 µg to 500 µg or 1 g. As described herein above, higher and lower concentrations are envisaged and dosage regime will be determined by an attending physician or veterinarian.

In a preferred embodiment said effective dose is administered before and/or during and/or after kidney surgery and/or dialysis. Preferably, said administering is within an hour and/or 1 to 24 hours and/or a day and/or 1 to 7 days and/or weekly and/or 1 to 4 weeks and/or monthly and/or bimonthly and/or quarterly and/or tri-annually and/or semi-annually and/or annually before and/or after kidney surgery and/or dialysis. Yet, said administering may also be before and/or during and/or after other treatment for insufficiency of kidney function.

A yet further subject matter of the present invention is a method for the production of a pharmaceutical composition for treating, preventing and/or delaying a renal dysfunction/failure in a mammal by combining a vector comprising a nucleic acid molecule encoding a functional Pax2 protein with a biologically acceptable carrier, wherein said nucleic acid molecule in said vector is placed under the control of an expression control sequence. Such control sequence are well known in the art and described, inter alia, herein above.

The specific embodiments as described herein above for the method for treating, delaying and/or preventing a renal dysfunction/failure in a mammal or the specific embodiments of the use of the present invention also apply for said method for the production of a pharmaceutical composition.

The present invention also relates to a method for converting mesenchymal tissue into an epithelial tissue comprising the administration of an effective amount of a substance capable of inducing and/or enhancing Pax2 expression in said mesenchym. Said substance may be administered to a tissue culture or to an animal, preferably a mammal and most preferably a human.

All the specific embodiments are described herein above for a substance capable of inducing and/or enhancing Pax2 expression apply, mutatis mutandis for the method for converting mesenchymal tissue into an epithelial tissue. Said method may be employed in vivo as well as in vitro.

Additionally, the present invention relates to a method for the regeneration of renal stem cells comprising the administration of an effective amount of a substance capable of inducing and/or enhancing Pax2 expression.

In the above methods said tissue(s) and stem cells, respectively, are mammalian, preferably human tissue(s) and stem cells or derived therefrom. The term "derived therefrom" is intended to mean in this regard that said cell or tissue has a precurser cell that is a mesenchymal tissue cell or a renal stem cell and essentially retains the biological characteristics of said cell or tissue.

The specific embodiments described for the methods for treating, delaying and/or preventing renal dysfunction/failure in a mammal or the specific embodiments of the use of the present invention apply also for said method for the regeneration of renal stem cells. This regeneration may be, inter alia, be achieved by induction/reactivation of dormant, renal stem cells. It had been shown, that animals which received a sublethal, but toxic dose of tunicamycin show a reduced rate of regeneration of epithelial cells of the proximal tubulus and a reduced rate of apoptosis. Therefore, and without being bound by theory, said regeneration by inducing and/or enhancing Pax2 expression may be achieved by activation of proteins of the apoptosis pathway.

The present invention further relates to methods for diagnosing renal dysfunction/failure and/or kidney function and/or dysfunction/failure or susceptibility thereto in a mammal comprising (a) determining the level or status of Pax2 mRNA kidney cells of said mammal; or (b) determining the level or status of Pax2 protein in kidney cells of said mammal; or (b') determining the level or status of Pax2 mRNA and the level or status of Pax2 protein in kidney cells of said mammal; and (c) comparing said level or status of Pax2 mRNA or Pax2 protein or Pax2 mRNA and Pax2 protein with the corresponding level in normal kidney cells; wherein the term "level" denotes the amount of mRNA or protein produced; and, the term "status" includes that the Pax2 gene, mRNA, protein or a transcription control element, including a promoter/enhancer sequence, may bear a mutation, deletion or any other modifications which would affect the overall activity of the gene when compared to the wild-type normal gene product, including post-translational modifications of the protein; and, the comparing indicates whether the Pax2 protein or the Pax2 mRNA or Pax2 protein and Pax2 mRNA are present or active above or below the Pax2 protein or Pax2 mRNA or Pax2 protein and Pax2 mRNA in normal cells to thereby provide the status in kidney cells.

Most preferably said renal dysfunction/failure and/or kidney function and/or dysfunction and/or failure or susceptibility thereto comprises acute tubular necrosis or susceptibility thereto.

In a most preferred embodiment of the method of the invention, said method is performed before and/or during and/or after kidney surgery and/or dialysis.

Preferably, said method is performed within an hour and/or 1 to 24 hours and/or a day and/or 1 to 7 days weekly and/or 1 to 4 weeks and/or monthly and/or bimonthly and/or quarterly and/or tri-annually and/or semi-annually and/or annually before and/or after kidney surgery and/or dialysis. Said method is preferably before and/or during and/of after treatment for insufficiency of kidney function.

In a most preferred embodiment of the methods described herein the mammal is a human.

Furthermore, the invention relates to the use of an effective dose of a substance capable of inducing and/or enhancing Pax2 expression in a mammal for the preparation of a pharmaceutical composition for treating, preventing, or delaying a renal dysfunction/failure in a mammal. Said mammal is preferably a human.

Additionally, the present invention provides a method for converting mesenchymal tissue into an epithelial tissue comprising the administration of an effective amount of a substance capable of inducing and/or enhancing Pax2 expression in the mesenchym and for a method for the regeneration of renal stem cells comprising the administration of an effective amount of a substance capable of inducing and/or enhancing Pax2 expression.

The invention also relates to a method for the regeneration of renal stem cells comprising the administration of an effective amount of a substance capable of inducing and/or enhancing Pax2 expression. Preferably, said tissue and stem cells, respectively, are mammalian, preferably human tissue and stem cells or derived therefrom.

The figures show:

FIG. 1: Time course of creatinine values in the early phase of acute tubular necrosis. Blood samples were drawn from mice until 72 hours after injection of folic acid (250 mg/kg body weight) versus control solution (300 mM bicarbonate). Bars represent mean serum values (n=2 for every time point) ±SEM. In the control group (■) there was no alteration of the serum creatinine levels after injection, while in the experiment group (○) there was a 4-5 fold increase in creatinine levels after folic acid injection up to 72 h.

Figure 2:
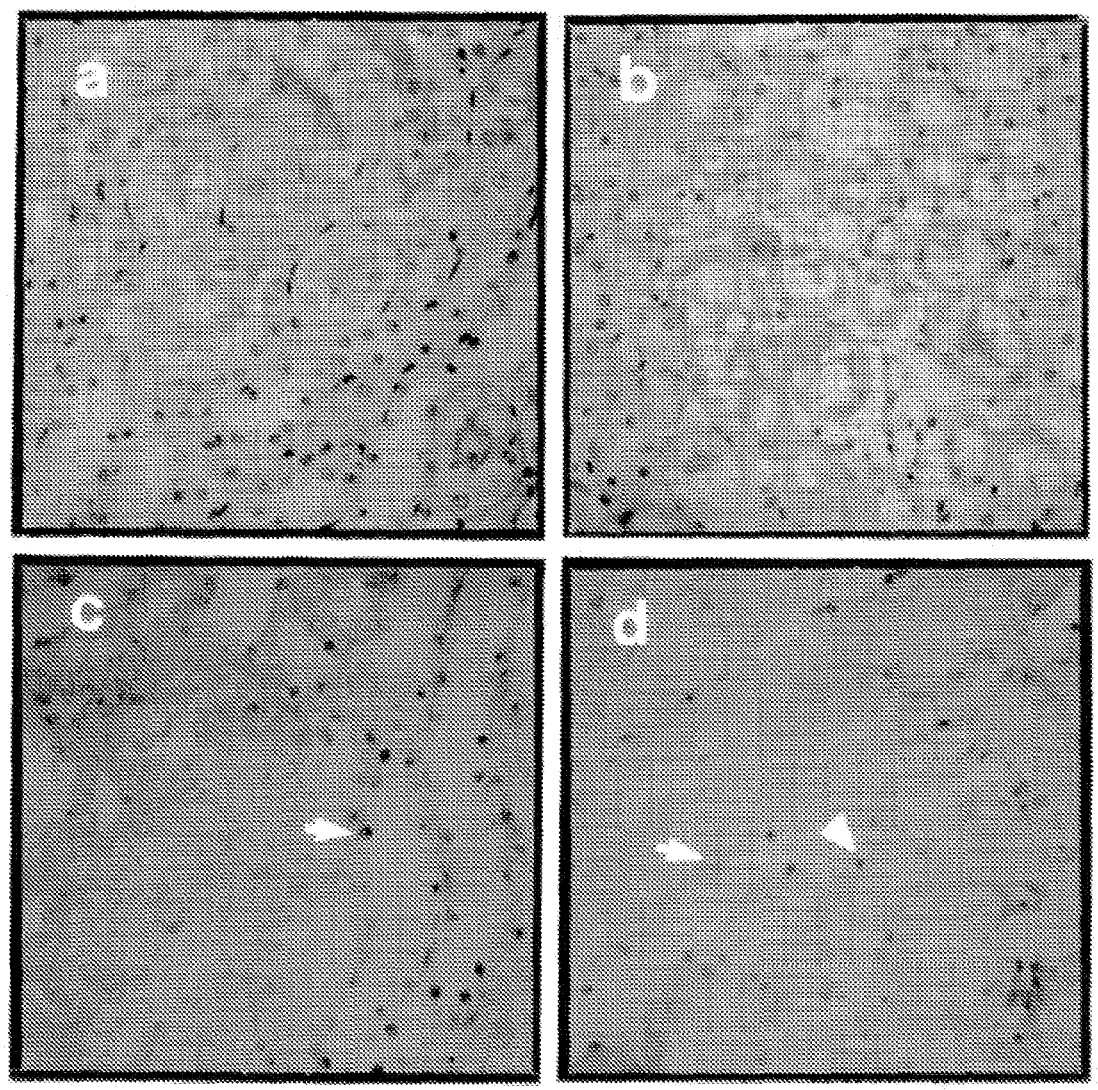

FIG. 2: PAS staining and in situ hybridization for Pax-2 mRNA in murine kidney sections. (a,b) Histologic damage documented by PAS staining of kidney sections 24 h after folic acid versus control injection (bars, 16 µm). (a) Kidney sections 24 h after sodium bicarbonate administration with regular glomeruli and proximal tubules. (b) Straight segments of proximal tubules show a disrupted brush border and a flattening of epithelia 24 h after folic acid administration indicating tubular damage. (c,d) In situ hybridization for Pax-2 mRNA in kidneys undergoing ATN versus control kidneys (bars, 25 µm). (c) A kidney section 24 h after sodium bicarbonate administration with a positive nuclear signal only in collecting ducts (arrow). (d) A kidney section 24 h after folic acid administration with positive signals in nuclei of damaged tubules (arrowhead) in addition to collecting ducts (arrow).

Figure 3:
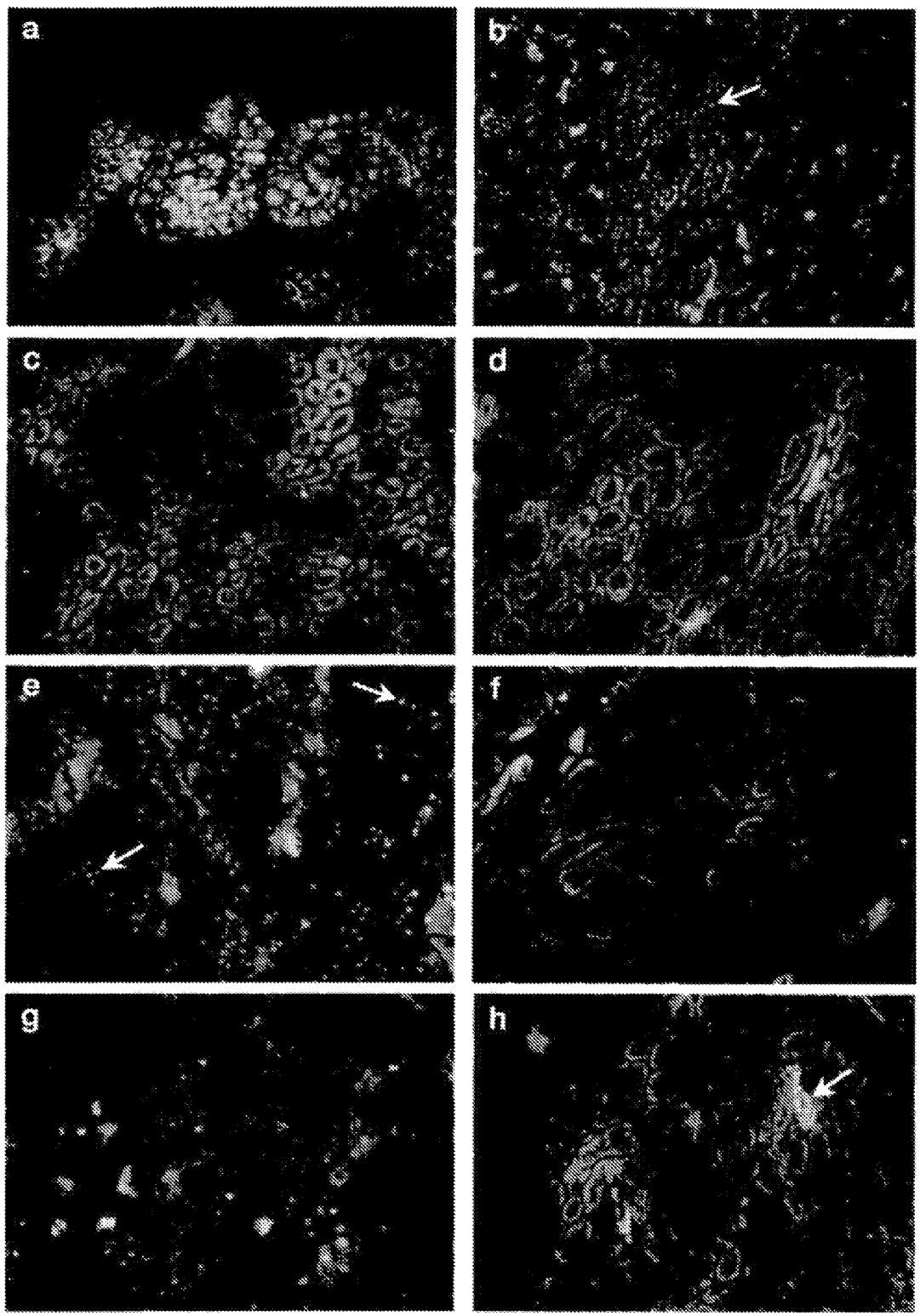

FIG. 3: Pax-2 immunofluorescence of cryosections from murine kidneys undergoing ATN. A murine neonatal kidney (E19) stained with anti-Pax-2 antibodies served as a positive control for Pax-2 expression. (a) In the neonatal kidney (E19) sharp boundaries exist between positively and negatively staining substructures. Nuclear localization of Pax-2 protein can be observed in cells of the ureter (u), s-shaped bodies (s) and comma-shaped bodies (c), while the surrounding tissue, the uninduced mesenchyme, is devoid of Pax-2 protein (bar, 16 µm). (b,c) Cryosections of a healthy adult mouse kidney stained with anti-Pax-2 antibodies. (b) In the papillary region Pax-2 can only be detected in the nuclei of the collecting duct cells (arrows; bar, 50 µm). (c) No signal can be detected in the tubular cells of the cortex of a healthy murine kidney (bar, 50 µm). (d) At 3 h after injection of folic acid there is no change for Pax-2 staining as compared to the zero time point (bar, 50 µm). After 6 h there is still no change of the immunofluorescence pattern in the folic acid or the control group (data not shown). (e) A marked re-expression of Pax-2 by immunofluorescence can be observed 24 h after folic acid injection in proximal tubular cell nuclei (arrows), while no change is noted in other parts of the nephron (bar, 50 µm). (f) In controls, no re-expression of Pax-2 can be observed after 24 h (bar, 50 µm). (g) 72 h after folic acid administration the Pax-2 immunofluorescence has markedly decreased in proximal tubular cell nuclei (bar, 25 µm). The expression pattern resembles the one observed in the control group (h, arrow indicating a collecting tubule positive for Pax-2; bar, 50 µm).

Figure 4:
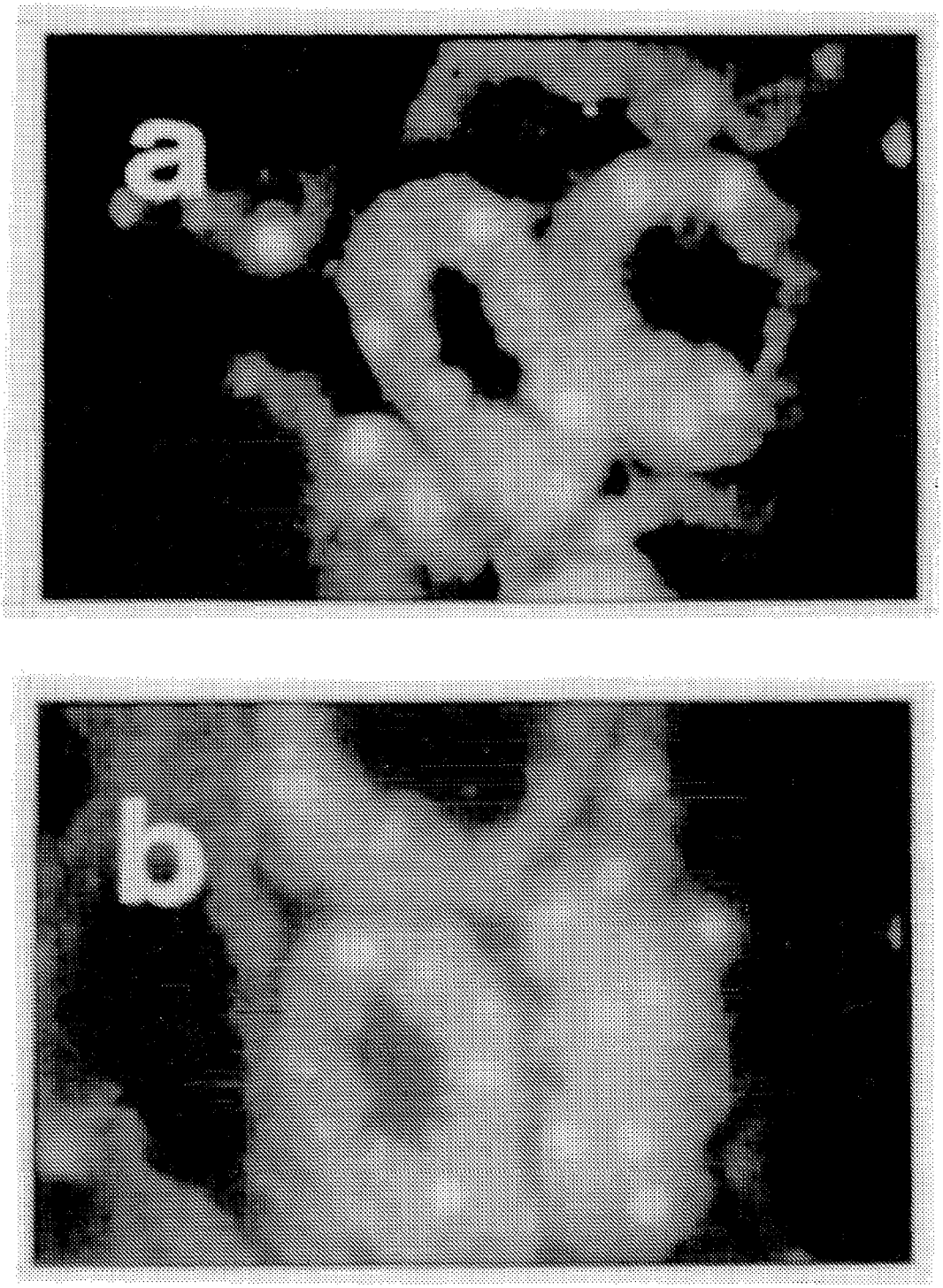

FIG. 4: Murine kidney cryosections of two different animals (a,b) obtained 24 hours after folic acid injection. Both cryosections were incubated with a Pax-2 antibody. A nuclear expression pattern of Pax-2 protein is detectable in proximal tubular cells. Bars, 10 µm.

Figure 5:
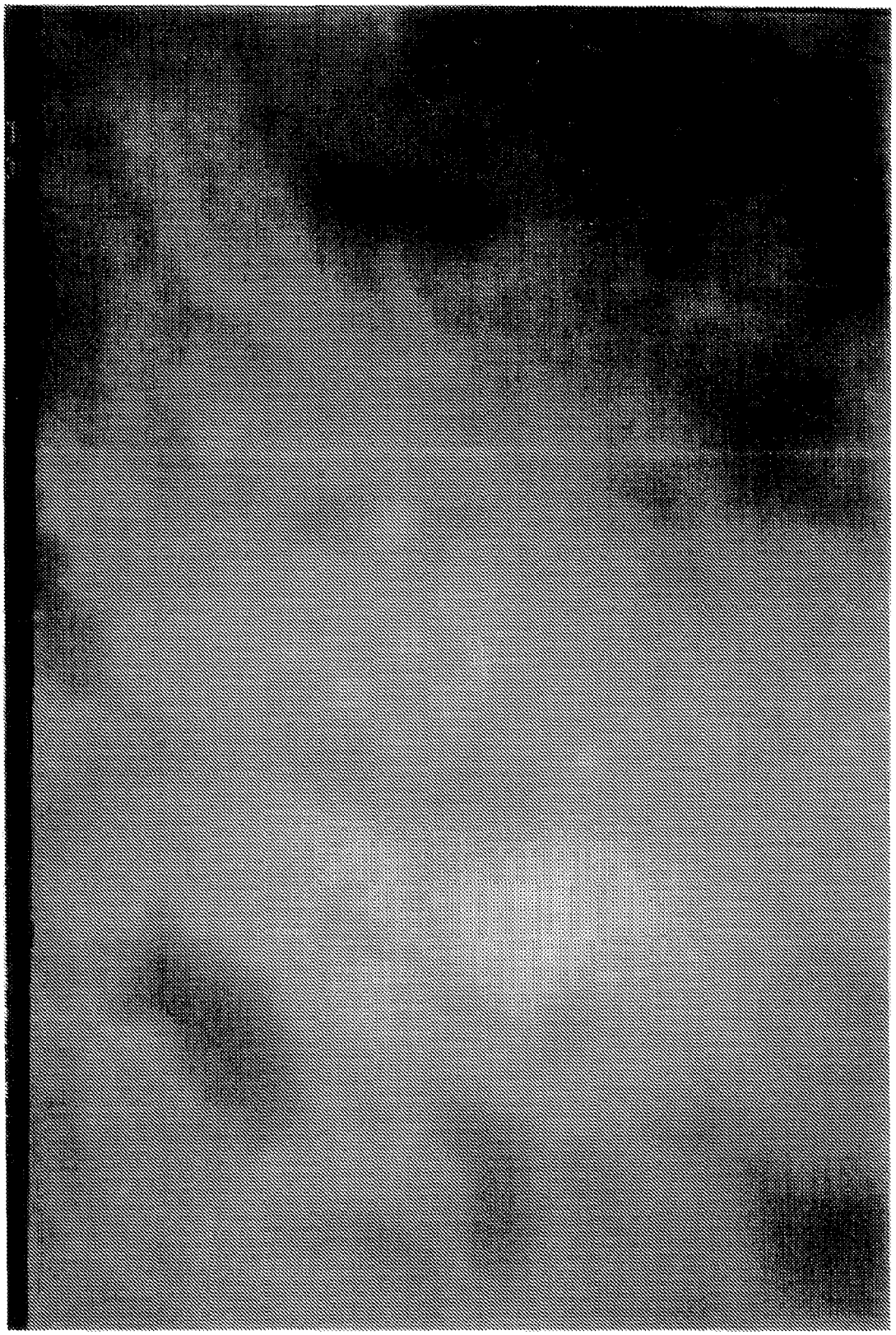

FIG. 5: Vimentin and Pax-2 coexpression in proximal tubes.

Figure 6:
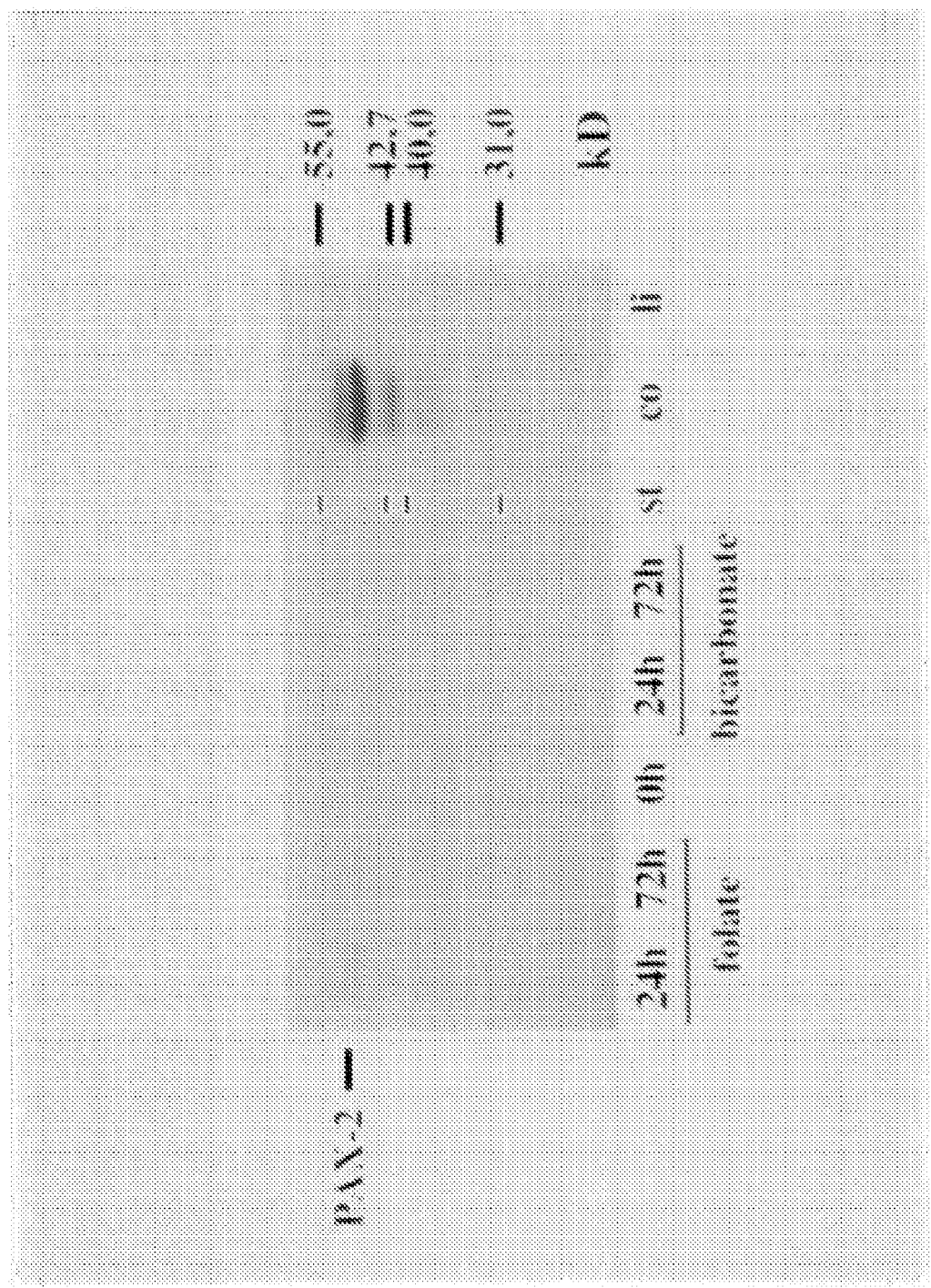

FIG. 6: A western blot for Pax-2 in protein extracts from cortical kidney sections obtained at different time points after injection of folic acid versus control solution (bicarbonate). In the positive control (co, embryonic murine kidney of developmental day 15) two bands can be detected with a molecular weight of 46 and 48 kD, respectively. In the negative control (li, adult murine liver) no specific bands are observed after incubation with anti-Pax-2 antibodies. The lanes termed "folate" were loaded with homogenates of kidneys from mice sacrificed at the indicated time points after folic acid injection. The control group ("bicarbonate") received bicarbonate injections as control. In the murine kidney homogenate at time point 0 h a band of 46 kD weight is seen. 24 h after folic acid injection the intensity of this band shows an increase, indicating increased Pax-2-protein concentration. The Pax-2 band has declined in kidney homogenates obtained 72 h after folic acid injection. The intensity of the Pax-2 bands in the control injected group (24 and 72 h after bicarbonate injection) is much lower than the intensity of the band 24 h after folic acid injection. 60 µg protein was loaded per lane, except of the positive control, where 10 µg was loaded.

Figure 7:

FIG. 7: RT-PCR for Pax-2 from RNA of cortical kidney sections after folic acid induced ATN. As a control the levels of adenine nuclear carrier (ANC) mRNA was examined, which is not differentially expressed after proximal tubular damage. Pax-2 mRNA shows an increase after folic acid injection with a maximum at 24 h after induction of ATN.

The invention will now be described by reference to the following biological examples which are merely illustrative and are not to be construed as a limitation of scope of the invention.

EXAMPLE 1

Determination of Functional and Histological Damage

The induction of renal damage by i.p. folic acid injection was verified by the observed rise of serum creatinine and BUN levels as coarse indicators of renal function (the time course of creatinine values is shown in FIG. 1).

In order to provoke ATN, 12 male CD-1 mice (Charles River Breeding Laboratories, Willmington, Mass.) weighing 30±5 g received 250 mg/kg body weight folic acid dissolved in 0.5 ml 300 mM sodium bicarbonate solution by i.p. injection. 14 mice were used as negative controls and received 0.5 ml 300 mM bicarbonate solution only. Three mice were sacrificed by cervical dislocation immediately after administration of bicarbonate solution at time point zero. At each time-point (after 3, 6, 24 and 72 h) and for each group (folic acid or bicarbonate injection) 3 mice were sacrificed, except at 72 h after bicarbonate injection, when only 2 mice were sacrificed. Kidneys were quickly removed and one was shockfrozen in liquid nitrogen while the other was processed for histological evaluation.

Blood was obtained by aspiration from the left ventricle to measure serum levels of creatinine and BUN using a Kodak Ektachem 500 Analyzer (Kodak, Rochester, N.Y.).

Both creatinine and BUN increased about 4-5 fold during the early phase of ATN (24-72 h after folic acid injection). No alteration of creatinine and BUN levels was observed up to 72 h after control injections with bicarbonate solution. The animals of the folic acid group started to show signs of disease at 12-24 h after folic acid injection, like fatigue, reduced alertness and bristling of the coat. These signs were absent in the control injected group. All animals survived up to the planned time-point of sacrifice.

PAS-staining of kidney sections after chemically induced damage showed alterations in kidney morphology consistant with ATN such as disrupted brush borders and flattening of epithelia (FIG. 2a,b). In summary, injection of folic acid resulted in the expected functional and morphological alterations of ATN with transient impairment of kidney function. No changes were observed in the vehicle injected control mice.

EXAMPLE 2

Studies Documenting Pax2 Expression after Provoked ATN 2.1 Indirect Immunofluorescence Studies For evaluation by light microscopy kidneys were fixed in 4%-paraformaline at different time points after the injection of either folic acid or control solution. 7 µm thick sections were cut on a microtome (Rotationsmikrotom 3455 Leitz, Leica, Bensheim, Germany) and PAS-staining was carried out to document histologic damage.

For indirect immunofluorescence studies 3-4 mm thick frozen mouse kidney sections were covered with Tissue Freezing medium (Leica, Bensheim, Germany) and frozen on dry ice. Cryostat sections (Kryotom Jung CM 3000, Leica, Bensheim, Germany) were cut at 7 µm thickness, collected on gelatinized slides and air dried for 60 min. The production and specificity of the polyclonal Pax-2 antibody has been described (Dressler, 1992, *Proc Natl Acad Sci* 89:1179-1183; Pueschel, 1992, Mech Dev 38:197-208). Cryosections were fixed in 3% paraformaldehyde in buffer A (1× PBS/0.05% Tween 20) at room temperature for 10 min. After washing with buffer B (1× PBS/0.1% Triton-X-100) for 10 min and buffer A for 5 min a preincubation of the sections with 15% goat serum (Gibco, Pairley, UK) was carried out in a moist chamber for 10 min at room temperature to reduce unspecific background staining. Afterwards sections were incubated with 80 ml of a 1:100 dilution of the polyclonal anti-Pax-2-antibody (0.8 µg/µl) in buffer C (buffer A/2% goat serum) for 15 h at 4° C. After two washing steps in buffer A for 5 min sections were again preincubated with 15% goat serum in buffer A. The secondary antibody (goat-anti-rabbit, TRITC-conjugated, Sigma, Deisenhofen, Germany) was centrifuged at 15000 g for 2 min and then diluted 1:50 in buffer C, placed on each section and incubation was carried out for 5 h at 4° C. After three washing steps for 5 min in buffer A sections were mounted in gelvatol (Airvol, Air products and Chemicals, Inc.; Utrecht, NL) with 2.5% DABCO (Sigma, Deisenhofen, Germany), which retarded quenching of the fluorescence. Sections were examined by a fluorescence microscope (Leitz DMRD, Leica, Bensheim, Germany) and photographed using a Kodak Ektachrome film (Rochester, N.Y.).

Tissue sections were also incubated with a monoclonal anti-vimentin antibody (Dianova, Heidelberg, Germany); a Cy2 (Dianova)-conjugated secondary antibody was used for fluorescence detection.

Indirect immunofluorescence studies were carried out on cryosections of murine kidneys obtained at different time points after injection of folic acid. The expression pattern of the developmentally expressed gene Pax-2 was observed using a polyclonal antibody. Pax-2 is expressed in cells of the comma- and s-shaped bodies, which are epithelial precursors of the developing proximal tubules, and this expression is downregulated as the kidney matures. In our study we used as a positive control a cryosection of an embryonic mouse kidney of later gestation at E 19 (FIG. 3a), where differentiation and epitheliogenesis is still present. Here a strong positive signal is observed in certain substructures of the developing kidney after incubation with the anti-Pax-2 antibody. Pax-2 protein was detected in cells of the ureter epithelium and in cells of the s- and comma-shaped bodies. The staining pattern is exclusively nuclear showing sharp boundaries between positive and negative areas.

ATN produced by the i.p. injection of folic acid into mice leads to an altered expression pattern of Pax-2 protein in the kidney. In the healthy adult kidney (time point 0 h), Pax-2 could be only detected in collecting duct nuclei, with the highest expression in the papilla (FIG. 3b). Cells of the proximal tubules or glomeruli were devoid of Pax-2 protein expression. Therefore, there was only little staining in the cortex (FIG. 3c).

No change of Pax-2 expression was observed at 3 h after folic acid administration (FIG. 3d). In contrast, at 24 h after folic acid injection a marked re-expression of Pax-2 protein was observed in proximal tubular cell nuclei (FIGS. 3e and 4). This result was obtained for all the animals of the group (n=3). The positive cells could be identified as belonging to regenerating proximal tubules due to the high-prismatic epithelium and due to remnants of the damaged brush border, which could be detected in the lumen of the tubules. Pax-2 concentration in proximal cell nuclei subsequently decreased and at 72 h after injection of folic acid Pax-2 was barely detectable in proximal tubules since expression became again restricted to collecting duct cells (FIG. 3g). In control bicarbonate injected animals, no increase of Pax-2 protein expression in proximal tubular cells was observed at any time point examined (FIG. 3f: 24 h after control injection, 3 h: 72 h after control injection). Pax-2 remained detectable exclusively in collecting duct cells.

Pax2 remained detectable exclusively in collecting duct cells in the control animal. Vimentin was detected and coexpressed with Pax2 in folic acid-injected animals 24 hours after injection (FIG. 5). No expression could be observed in control injected animals.

2.2 Western Blot

To complement the increase of Pax-2 immunofluorescence in proximal tubular cells after folic acid induced ATN, we examined Pax-2 protein concentration in kidney homogenates by the semi-quantitative method of western blotting (FIG. 6). In E15 embryonic mouse kidney homogenates, which served as positive controls, three bands could be detected with molecular weights of 42, 46 and 48 kD, respectively. The intensity was strongest in the 46 kD band, which corresponds to the Pax-2b isoform, which is most abundant in vivo (Dressier, 1992 loc. cit.). In the negative control, which consisted of a murine liver homogenate, no specific bands could be observed. To analyze the effect of folic acid induced ATN, cortical kidney sections were extracted directly after the sacrifice of the animals and blotted with anti-Pax-2 antibodies. To minimize the possible contaminating effect of the basal expression of Pax-2 protein in the normal papillary region (see FIG. 3b), which had to be distinguished from newly synthetized Pax-2 protein in the cortex, total cell extracts including the nuclear proteins of thin cortical sections of murine kidneys were examined. In the control kidney cortex homogenate (time point 0 h), a very weak positive band is observable at 46 kD molecular weight. This probably represents the Pax-2 protein present in collecting ducts derived from cortical sections as determined by indirect immunofluorescence. Comparable to the increase of Pax-2 protein in proximal tubules observed by indirect immunofluorescence studies 24 h after ATN, an increase of Pax-2 protein levels was detectable by western blotting of cortical homogenates. The upregulation of Pax-2 protein expression was temporary. 72 h after the induction of ATN the intensity of the Pax-2 band at 46 kD declined. In comparison to the Pax-2 band 24 h after kidney damage, the bands of the control group (24 h and 72 h after bicarbonate injection) showed a much weaker intensity.

2.3 In situ Hybridization

In the healthy adult murine kidney Pax-2 mRNA is detectable exclusively in the nuclei of collecting duct cells and to-a smaller extent in the cells of the distal tubules. No Pax-2 positive cells could be detected in control proximal tubules 24 h after bicarbonate injection (FIG. 2c). Contrary, 6 h and 24 h after folic acid injection proximal tubular epithelia of the outer medulla and inner cortex showed a spotty nuclear signal for Pax-2, that was most pronounced in damaged epithelia (FIG. 2d). 72 h after folic acid injection this could only rarely be observed. The fact, that Pax-2 mRNA was detectable only in the nuclei, but not in the cytoplasm of damaged cells could be due to a short half-life of the Pax-2 mRNA. A sufficient amount of Pax-2 mRNA to be detectable by in situ hybridization would then be expected to be present only at the place of its origin, in the nucleus.

2.4 RT-PCR Studies

A specific band of the expected size for Pax-2 could be detected in quantitative RT-PCR experiments of RNA from cortical mouse kidneys in control as well as in experimental animals. In the folic acid injected group, there was a 2-3 fold increase in the intensity of the signal 24 h after injection compared to the 0 h-value (FIG. 7) or the-control-injected animals (data not shown). No change was observed in mRNA for ANC as a control housekeeping gene not affected by ATN (23). Thus, the increase in Pax-2 protein is also accompanied by an increase of Pax-2 mRNA.

2.5 Conclusion

In conclusion, Pax2 is known to play a crucial role during early metanephric kidney development. A close timely correlation between the impairment of kidney function and the re-expression of Pax-2 in regenerating tubular epithelium was observed. After kidney injury Pax-2 was locally restricted reexpressed in regenerating proximal tubules. This re-expression was maximal 24 h after folic acid injection. Similar to its transient expression pattern during development (Dressier, 1992 loc. cit.; Eccles, 1992, *Cell Growth Differ* 3:279-289) expression in proximal tubular cells declined after reconstitution of the tubuli, beginning 72 h after induction of ATN. This transient re-expression of Pax-2 in hyperproliferative proximal tubular epithelia after ATN is paralleled by the findings of Winyard et al. (Winyard, 1996, *J Clin Invest* 98:451-459), which showed overexpression of Pax-2 in cystic and hyperproliferative dysplastic epithelia in human kidney malformations. It is suggestive that the transient expression of Pax-2 after ATN is a physiologic process meeting the need for a timely restricted hyperproliferative state of the proximal tubule. Contrary, deregulated Pax-2 expression may lead to tubular malformations due to uncontrolled hyperproliferation, both in human disease (Winyard, 1996 loc. cit.) and during murine embryonic development (Dressler, 1993, *Nature* 362:65-67). High expression levels of Pax-2 have also been shown to be present in malignant tumors like Wilms tumor (Dressier, 1992 loc. cit.) and renal cell carcinoma (Gnarra, 1995, *Cancer Res* 55.4092-4098). Furthermore, several members of the Pax family including Pax-2 have oncogenic potential (Maulbecker, 1993, *Embo J* 12:2361-2367).

By immunofluorescence studies, possible changes in the expression patterns of other developmentally expressed genes, including WT1, GDNF, c-ret and N-myc were also examined. Contrary to the finding with Pax-2 no change in localisation or intensity of the expression of these genes was observed until 72 h after folic acid injection.

EXAMPLE 3

Induction of ATN and Inhibition of Pax2 Expression

Induction of ATN was carried out as by injection of folic acid and Pax2 expression was inhibited by an antisense approach.

3.1 Determination of Physical Behaviour of Treated Mice

10 FVBN mice (Charles River Breeding Laboratories) weighing 20±5 g received 250 mg/kg body weight folic acid dissolved in 0.3 ml 300 mM sodium bicarbonate solution by i.p. injection. 5 of those mice were simultaneously i.p. injected kontralaterally with 1.25 mg/kg bw of phosphorotioated substituted antisense Pax2 DNA (sequence: AS17: 5'-ggg Agg CCg TgC Tgg gAA C-3'; as described by Rothenpieler and Dressler, 1993) while the 5 other mice were injected also simultaneously with 2.50 mg/kg bw of phosphorothioated antisense Pax2 DNA. DNA was dissolved prior to i.p. injection into a total of about 350 µl OPTI-MEM (Gibco-BRL). To enhance uptake of the oligos we used Lipofectamine (Gibco-BRL) in conjunction with the oligos in a concentration of 0.8 mg/mg DNA. 10 additional mice (5 each) were used as controls and received either 0.3 ml 300 mM bicarbonate solution (negative) or 250 mg/kg body weight folic acid (positive). Two additional mice were sacrificed by cervical dislocation immediately after administration of bicarbonate solution at time point zero. All other mice were sacrified after 24 h or 48 h and checked for Pax2 protein expression. Kidneys were quickly removed and shockfrozen in liquid nitrogen or stored at −80° C. for further evaluation.

Besides those mice dedicated for western blotting two additional mice were coinjected with Pax2-AS-ODN (2.5 mg/kg bw) and folic acid (250 mg/kg bw) to determine the influence of antisense-Pax2-ODNs on long term survival (prospected observation period 14 days).

The animals injected with folic acid (without Pax2-Antisense ODNs) started to show signs of disease at 12-24 h after injection, like fatigue, bristling of the coat and reduced alertness. The same behaviour was observed in animals which were coinjected with Pax2-Antisense ODNs. Those signs were absent in the control injected group (bicarbonate).

Besides the 10 animals which were coinjected with antisense Pax2-ODNs and folic acid and sacrificed 24 resp. 48 h after injection, we followed the behavior and physical state of 2 mice which were treated with the same regimen but not sacrificed. Both animals died around day 10.

3.2 Western Analysis

For western blotting analysis thin cortical sections (about 1 mm thick) were homogenized in a glass-homogenizer with boiling extraction buffer (62.5 mM TRIS, pH 6.8; 1% sodium dodecyl sulfate; 10% Glycerol; 5% β-mercaptoethanole). Homogenates were incubated at 95° C. for 15 min and centrifuged (15000 g) for 10 min. in an Eppendorf microcentrifuge at 4° C. Supernates were further analyzed. After determination of protein concentrations with the BioRad Dc ProteinAssay (BioRad, Hercules, Calif.) concentrations were standardized and aliquots stored at −80° C. Western blotting was done as described by Harlow and Lane (1988). Between 60-100 µg protein per lane was loaded. After electrophoresis and electroblotting the PVDF membrane (DuPont) was preincubated in methanol and TBST. Blocking was done with 5% nonfat dry milk in TBS. The polyclonal Pax-2 antibody (5.0 µg/µl) was used in a 1:5000 dilution in TBT+1% milk in TBS+0.5% Tween and incubated at room temperature for 2 hours. After three washing steps for each 10 min. in 1× TBS/0.5% Tween 20/1% milk the secondary antibody (goat-anti-rabbit, horseradishperoxidase (HRP) conjugated) was added in a dilution of 1:5000 in 1× TBS/0.5% Tween 20/1% milk for 1 h. After three washing steps for 10 min. each in TBSTM and two washing steps in 1M TBS detection of specific bands was carried out using the enhanced chemoluminescent (ECL) detection kit (NEN Life Science, Boston, Mass.) and Kodak detection film.

Pax2 protein concentration was determined by the semi-quantitative method of western blotting. In mouse kidney homogenates, which served as positive controls (folic acid injected), a clear Pax2 band was detected with the molecular weight of approximately 46 kD. Mice serving as negative controls (bicarbonate injection) did not display any Pax2 band. Mice which were coinjected with antisense Pax2-ODNs showed a significant reduction of the signal at the 46 KD level in both antisense injected groups (1.25 and the 2.5 mg/kg bw aS-Pax2).

EXAMPLE 4

Phenotypic Conversion of Mesenchymal Cells to Epithelium by Pax2

In order to examine further the role of Pax2 in ATN and/or other kidney dysfunctions/failures and in order to establish a successful gene transfer approach, Pax2 expression and its physiological consequence was examined by gene transfer studies into uninduced metanephric mesenchyme.

To address whether Pax2 is sufficient to induce epithelial cell differentiation from the metanephric mesenchymal cells of the intermediate mesoderm in the absence of induction, we utilized gene transfer methods to introduce Pax2 expression vectors into primary metanephric mesenchyme cultures. A series of retroviral vectors were designed to express either the Pax-2a or Pax-2b alternatively spliced forms. In particular, transducing retroviruses were constructed by inserting either the entire Pax-2a or Pax2b (Dressier (1990) loc. cit.) coding region (NotI-HindIII) into the unique SalI site of the viral vector pMMuLV-SVTK-NEQ (Rubenstein (1984) Proc. Natl. Acad. Sci. USA 81,. 7137-7140). The recombinant viral vectors were transfected into PA317 cells using calcium phosphate methods. And subjected to G418 selection using 400 μg/ml. Media from resistant colonies was assayed for virus production by infecting NIH 3T3 fibroblasts and selecting with 400 μg/ml G418. Resistant 3T3 cells were clonally isolated and assayed for Pax-2 protein expression by western blot analysis. The kidneys were microdissected from embryos in Hams F10 media at room temperature. Metanephric mesenchyme was isolated from E11 kidneys by incubation in PBS containing 0.1M EDTA for 4 min. and microdissected with 30 ga. syringe needles. The mesenchymes were rinsed in DMEM supplemented with 10% fetal calf serum and placed in conditioned media from PA317 cells producing either the retrovirtal vector (RV-vector) or the Pax2 transducing virus (RV-Pax2). Polybrene was added to 16 μg/ml to aid in virus adsorption. After 2 h, the mesenchymes were rinsed in fresh media (DMEM+10% FCS) and cultured for an additional 24 h on a 1.0 mm pore size nuclepore filter suspended by stainless steel wire grid over a monolayer of PA317 virus producing cells. 4-6 mesenchymes were combined in a single aggregate. Cultures were frozen after 5 days while still attached to the filter and sectioned in a cryostat.

The alternative splice forms differ by the addition of a 23 amino acid encoding exon (Pax-2a) that does not alter the downstream reading frame. No functional differences between Pax-a and Pax-2b have been detected to date (Lechner (1996), J. Biol. Chem. 271, 21088-21093). The viral vectors were transfected into the amphotropic producer line PA317 and the conditioned media used to infect NIH 3T3 for titration. Correct expression of the proteins could be assayed in infected NIH 3T3cells using Pax-2 specific antibodies. Initial experiments utilized metanephric mesenchyme from wild type E11 mouse kidneys had been microdissected from the ureteric bud after EDTA treatment. Isolated mesenchymes were grouped into aggregates of 4-6 and cultured on nuclepore filters on stainless steel grids in the presence or absence of Pax-2 retrovirus producing cell lines plated on the bottom of the dish. Aggregates co-cultured with Pax-2/PA317 cells consistently generated small epithelial cysts, usually not more than one per aggregate. Mesenchyme co-cultured with control PA317 cells generally flattened out and did not show evidence of epithelial cell formation. The mesenchymal aggregates were sectioned and stained for Pax-2 and for the early renal epithelial markers. Expression of the adhesion molecule E-cadherin and laminin was indicative of cell polarization and basement membrane formation. Occasionally, the basement membrane was located on the inside of the epithelial cysts indicating a reversal of cell polarity. Although the majority of mesenchymes cultured above the control PA317 cells did not show any sign of epithelium formation, one culture did express Pax-2 and E-cadherin. This was probably due to separation of the mesenchyme at a slightly later stage such that induced Pax-2 expressing cells had been exposed to the ureteric bud derived signal for a longer period of time.

To eliminate the possibility of contamination by induced mesenchyme that expresses the endogenous Pax-2 gene, the metanephric mesenchyme from Pax-2-/-mutant mice were utilized in subsequent experiments. Females from Pax-2 heterozygous mutant mating pairs were sacrificed after 11 days gestation and the embryos sorted by visual inspection Embryos exhibiting exencephaly of the midbrain-hindbrain region were dissected further and the metanephric mesenchyme isolated. The absence of the ureteric bud was noted and the body of the embryo utilized for DNA extraction to verify the Pax-2-/-homozygous genotype. The mutant mesenchymes were incubated with Pax-2 or control retroviral vectors as described above.

Metanephric mesenchymes were isolated from E11.5 embryos that showed severe hindbrain defects and had no evidence of ureteric bud growth. DNA was extracted from the anterior half of each embryo and genotyped by southern blotting to confirm the homozygous Pax-2-/-phenotype. Pax-2 homozygous mutant mesenchymes were cultured as before on filters suspended above the virus containing media. Transient traensfection of the mutant mesenchymes utilized Lipofectamine as follows: 4 μg of CMV-Pax-2b or CMV-vector DNA were mixed with 2 μg of Green Latern DNA in 0.3 ml of serum free DMEM. Subsequently, 15 μl of Lipofectamine in 0.3 ml of DMEM was added to the DNA and the mixture diluted into 2.4 ml of DMEM containing the mesenchymes. After 2 h of incubation at 37° C., the mesenchymes were removed, rinsed in PBS, and cultured on filters in DMEM, 10% FCS, 50 μg/ml transferrin.

After 4 days in culture the majority of mutant mesenchymes (6/9) cultured with Pax-2/PA317 cells showed evidence of epithelial cyst formation whereas all the mesenchymes cultured with control PA317 cells flattened out and died. As with the wild-type mesenchyme, sections through the mutant mesenchyme revealed the expression of E-cadherin on the cell surface and laminin along the basement membrane. Pax-2 expression could also be detected, albeit levels were lower than in the wild-type mesenchyme.

In addition to retroviral mediated gene transfer, we utilized plasmid DNAs and lipofectamine to express Pax-2 in homozygous mutant mesenchyme. The expression plasmid pCMV-Pax2b (Lechner (1996) loc. cit.) and control pCMV vectors were mixed with Green Fluorescent Protein (GFP) expression vector and introduced into isolated mesenchymal rudiments. After 2 or 3 days in culture, GFP could be visualized directly, indicating sucessful transfection. Cultures were fixed and stained whole mount with Pax-2 and E-cadherin antibodies. Confocal images reveal nuclear Pax-2 expression and cell surface E-cadherin on pCMV-Pax2b transfected cultures but not in controls (data not shown). As with the retroviral gene transfer Pax-2 expression was sufficient to convert the mesenchymal cells to an epithelial phenotype as evidenced by E-cadherin expression and basement membrane formation.

The invention claimed is:

1. A method for regenerating tubular epithelium in a mammal patient affected by acute tubular necrosis comprising administering directly to the kidney of said mammal patient a therapeutically effective amount of a composition comprising a vector comprising a nucleic acid molecule encoding Pax2a or Pax2b protein, wherein said nucleic acid molecule is operatively linked to an expression control sequence.

2. The method of claim 1, wherein said vector is an expression vector, a gene targeting vector or a gene transfer vector.

3. The method of claim 1, wherein said composition is administered by injection and said therapeutically effective amount is in the range of 1 µg to 5 g.

4. The method of claim 1, wherein said composition causes an increase in Pax2a or Pax2b expression in the cells of the proximal tubuli in the kidney of the patient.

5. The method of claim 1, wherein said patient is a human.

6. A method for generating epithelial cysts from mesenchymal cells in vitro comprising transforming said cells with a vector comprising a nucleic acid molecule encoding Pax2a or Pax2b protein, wherein said nucleic acid molecule is operatively linked to an expression control sequence.

7. The method of claim 6, wherein said mesenchymal cells are isolated from a mammal.

8. The method of claim 6, wherein said mesenchymal cells are isolated from a human.

* * * * *

UNITED STATES PATENT AND TRADEMARK OFFICE
CERTIFICATE OF CORRECTION

| | | |
|---|---|---|
| PATENT NO. | : 7,612,046 B2 | Page 1 of 1 |
| APPLICATION NO. | : 10/182680 | |
| DATED | : November 3, 2009 | |
| INVENTOR(S) | : Rothenpieler et al. | |

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by (230) days Delete the phrase "by 230 days" and insert -- by 559 days --

Signed and Sealed this

Tenth Day of August, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,612,046 B2 | Page 1 of 1 |
| APPLICATION NO. | : 10/182680 | |
| DATED | : November 3, 2009 | |
| INVENTOR(S) | : Rothenpieler et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 770 days.

Signed and Sealed this
First Day of January, 2013

David J. Kappos
*Director of the United States Patent and Trademark Office*